United States Patent [19]

Mitchell, III

[11] Patent Number: 4,473,505

[45] Date of Patent: Sep. 25, 1984

[54] PHOSPHINE AND PHOSPHONIUM COMPOUNDS AND CATALYSTS

[75] Inventor: Howard L. Mitchell, III, Baton Rouge, La.

[73] Assignee: Exxon Research and Engineering Co., Florham Park, N.J.

[21] Appl. No.: 423,641

[22] Filed: Sep. 27, 1982

Related U.S. Application Data

[62] Division of Ser. No. 120,937, Feb. 12, 1980.

[51] Int. Cl.³ .............. C07F 17/02; C07F 15/00; C07F 15/02
[52] U.S. Cl. .............. 260/439 CY; 260/429 R; 260/429.5; 260/439 R; 260/440; 260/441; 260/430; 260/438.1
[58] Field of Search .............. 260/429 R, 429.5, 440, 260/441, 543 P, 543 B; 568/2, 10, 9, 16; 556/405; 564/15, 8

[56] References Cited

U.S. PATENT DOCUMENTS

| | | | |
|---|---|---|---|
| 3,657,298 | 4/1972 | King et al. | 260/440 |
| 4,008,281 | 2/1977 | Knowles et al. | 260/429 R |
| 4,138,420 | 2/1979 | Unruh et al. | 260/439 CY |
| 4,152,344 | 5/1979 | Unruh | 260/439 CY |
| 4,201,714 | 5/1980 | Hughes | 260/439 CY X |
| 4,209,554 | 6/1980 | Traynor et al | 260/440 X |

FOREIGN PATENT DOCUMENTS 1160855 1/1964 Fed. Rep. of Germany.
859391 1/1961 United Kingdom.

OTHER PUBLICATIONS

Kosolapoff et al., Organic Phosphorus Compounds, Wiley-Interscience, N.Y., vol. 1, pp. 461, 475, 482, 484 (1972).
Chemical Communications, pp. 1559–1561 (1968), A. J. Carty et al.
Journal of Organometallic Chemistry, 50 (1973), 247–263, by H. A. Patel, A. J. Carty and N. K. Hota.
Chemical Abstracts vol. 80, 1974, p. 356, Zh. Obshch. Khim. 1974, 44(1), 103–106 (Russ).
Tetrahedron, vol. 27, pp. 3893 to 3907, 1971, "Interactions In Acetylenes".

*Primary Examiner*—Helen M. S. Sneed
*Attorney, Agent, or Firm*—Robert J. North

[57] ABSTRACT

Novel ligand materials and transition metal complexes thereof are disclosed which are useful as solvents and/or catalysts for various processes, including catalytic conversion processes for the conversion of hydrocarbons or carbon monoxide, such as the hydrocarbonylation of olefins, hydrogenation using $H_2$ or CO and $H_2O$, dehydrogenation, hydrocarbon synthesis, alcohol synthesis, and water-gas disproportionation catalysis. Among the novel ligand materials disclosed are compositions containing phosphine and arsine coordinating groups along with, e.g., groups comprising fluorines, ethynyl or ethenyl groups, quaternary ammonium, arsonium and/or phosphonium groups. Ligands containing M—O—L linkages and complexes thereof are also disclosed wherein M is selected from, for example, Si or Ti and L is selected from P or As. Also, various ion-exchanged ligand compositions, photoreactive compositions and the uses of such compositions are also described.

5 Claims, No Drawings

PHOSPHINE AND PHOSPHONIUM COMPOUNDS AND CATALYSTS

This is a division of application Ser. No. 120,937, filed Feb. 12, 1980.

TECHNICAL FIELD

The invention relates to ligand materials, solvents, and complexes used in hydrocarbon and carbon monoxide conversion reactions. More specifically, the invention relates to novel solvents, ligand materials, complexes, ion-exchanged ligand compositions and photoreactive compositions and to processes of using these materials, for example, in hydrogenation, dehydrogenation, hydrocarbonylation, hydrocarbon synthesis, alcohol synthesis and water-gas disproportionation catalysis.

BACKGROUND ART

Various ligands and catalysts are known for hydrocarbon and carbon monoxide conversion reactions. For example, rhodium catalysts containing triaryl phosphine ligands have been extensively used for hydroformylation reactions. Likewise, cobalt hydroformylation catalysis has been widely used commercially, but the addition of phosphine ligands has proven of only minor value in such reactions.

Transition metal complexes of both triphenylphosphine and trialkyl phosphine have been widely studied as catalysts for hydroformylation, hydrogenation, etc. For their application in reactions of carbon monoxide, particularly carbonylations, see the monograph of Juergen Falbe, "Carbon Monoxide in Organic Synthesis," Springer Verlag, New York, 1970. Also, general discussion of catalysis of reactions of carbon monoxide is included in "Homogeneous Catalysis Involving Carbon Monoxide" *Catalysis*, Vol. I, *Specialist Periodical Reports V*, The Chemical Society, Burlington House, London, 1977 by Davidson, et al. In the area of rhodium catalyzed hydroformylations of alpha-olefins, homogeneous catalyst systems employing triaryl phosphine and other trivalent phosphorus compounds in complex with rhodium plus excess phosphine ligand were described by R. L. Pruett and J. A. Smith in U.S. Pat. No. 3,527,809.

Certain transition metal complexes containing phosphines covalently anchored to polymeric substrates have also been disclosed as heterogeneous catalyst systems. Such polymer-anchored complexes were reviewed by C. C. Leznoff in Vol. III, pp. 65-85, of the *Chemical Society Review* in 1974. The polymer-anchored rhodium hydroformylation catalysts were also discussed in detail in the *Journal of Organometallic Chemistry*, Vol. 134, pp. 85-94, in 1977 by W. H. Lang, A. T. Jurezicz, W. O. Haag, D. D. Whitehurst and L. D. Rollmann. Other complexes covalently anchored to inorganic solids, such as silica, were disclosed in a number of U.S. patents such as U.S. Pat. No. 3,726,809 by K. G. Allum, S. McKenzie and R. C. Pitkethly and U.S. Pat. No. 4,151,114 by A. A. Oswald and L. L. Murrell.

Oswald in U.S. Pat. Nos. 4,136,103 and 3,929,849 discloses tetraakylphosphonium aluminosilicates and complexes thereof with group VIII transition metals, e.g., rhodium. There is no suggestion in these patents of using such catalyst in any hydrocarbon and carbon monoxide conversion processes.

Still other patents have described bis-phosphine compounds as complexes for rhodium. For example, Booth in U.S. Pat. Nos. 3,965,192 and 3,560,539 discloses ethylene bis-(diphenylphosphine) as a ligand for rhodium complexes.

McVicker in U.S. Pat. Nos. 3,939,188 and 3,946,082 discloses processes for preparing oxygenated products such as aldehydes and suggests as catalysts for his process zero valent rhodium complexes with various ligands thereon. As ligands for such complexes, McVicker suggests, for example, phosphine ligands with various substituents selected from a long list of possibilities among which are included halides such as fluoride, alkyl, alkoxy, cycloalkyl, cycloalkoxy, phenyl, phenyl substituted with halide, phenyl substituted with cycloalkyl, phenyl substituted with alkoxy, oxyphenyl, oxyphenyl substituted with alkyl, oxyphenyl substituted with cycloalkyl, oxyphenyl substituted with halide and oxyphenyl substituted with cycloalkoxy.

Kawse in U.S. Pat. No. 4,013,700 discloses a process for the manufacture of polyhydric alcohols and their ether and ester derivatives by reacting oxides of carbon and hydrogen in the presence of small amounts of a quaternary phosphonium cation and a rhodium carbonyl complex. Exemplary quaternary phosphonium cations for the Kawse process are described in Column 4, lines 8-41 of the patent.

Some of the latest advancements in Fischer-Tropsch and water-gas shift reactions are disclosed in "Advances in Fischer-Tropsch Chemistry" by M. E. Dry in *Ind. Eng. Chem., Prod. Res. Dev.*, Vol. 15, No. 4, 1976; "Reductions With Carbon Monoxide and Water in Place of Hydrogen. 1. Hydroformylation Reaction and Water-Gas Shift" by H. C. Kang, et al in *Journal of the American Chemical Society*, Vol. 99, pp. 8323-8324 (1977); and "Coal Research Shifts to Soluble Catalysts" in *Chemical Week*, Apr. 19, 1978, pp. 63 and 65. Advances in the use of silicate clusters are discussed in "New Silicate Has Cluster of Uses," *Chemical Week*, Mar. 7, 1979, pp. 37 and 38. Various aspects of the support of metal complex catalysts on metal oxide supports as well as the use of such materials in photo reactions are discussed in "Chemical Modification of a Titanium(IV) Oxide Electrode to Give Stable Dye Sensitisation Without a Supersensitiser" by S. Anderson, et al in *Nature*, Vol. 280, Aug. 16, 1979 and "Photoelectrochemical Conversion of Optical Energy to Electricity and Fuels," by M. S. Wrighton in *Accounts of Chemical Research*, Vol. 12, No. 9, pp. 303-310 (September, 1979). Other aspects of Fischer-Tropsch synthesis and similar reactions are discussed in "Carbon Monoxide-Hydrogen Reactions," by H. Pichler, *Kirk Othmer's Encyclopedia of Chemical Technology* (Second Edition), Vol. 4, pp. 446-489 (1964).

DISCLOSURE OF INVENTION

In accordance with the present invention, a series of novel solvents, ligand materials and transition metal complexes have been discovered which are particularly advantageous for use in catalytic conversion processes for the conversion of hydrocarbons and carbon monoxide to more desirable products.

One aspect of the present invention involves compounds containing ethynyl linkages. These ethynyl compounds are of the formulas $$R_{4-b}L^+[QC \equiv C(-J)]_c[-Q(-J)_a]_d \qquad 1$$

and

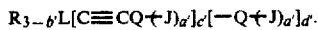
$$R_{3-b'}L[C\equiv CQ(+J)_{a'}]_{c'}[-Q(+J)_{a'}]_{d'}.\quad II$$

In these formulas, the symbols a and a' are integers of from 0 to 2, while b is an integer of from 1 to 4 and b' is an integer of from 0 to 3. The symbol c is an integer of from 1 to 4, while c' is an integer of from 1 to 3. The symbol d is an integer of from 1 to 3, and d' is an integer of from 0 to 2. The sum represented by the c+d equals b and the sum represented by c'+d' equals d'. Each L is independently selected from a trivalent P, As and N atom. Each R group is independently selected from the group consisting of alkyl, alkenyl, alkynyl, aryl, alkoxyalkyl, aryloxyalkyl, alkoxyaryl, aryloxyaryl, ferrocenyl, and fluoro groups, wherein the aryl portions thereof can be substituted with a halogen and the alkyl portions thereof can be substituted with a member selected from halogen and hydroxy groups, provided that said halogens on said alkyl groups are not in an alpha-position with respect to L atoms unless they are fluoro atoms. Each Q group is independently selected from the group consisting of alkyl, alkenyl, alkynyl, aryl, alkoxyalkyl, aryloxyalkyl, alkoxyaryl, aryloxyaryl, and ferrocenyl, wherein the aryl portions thereof can be substituted with a halogen and the alkyl portions thereof can be substituted with a member selected from halogen and hydroxy groups and wherein the Q groups have a+1 points of attachment to L atoms. Each J is selected from the group consisting of LR₂, LR—Q¹—LR₂, LR—Q¹—LR—Q¹LR₂, L+R₃, L+R₂—Q¹—L+R₃, L+R₂—Q¹—L+R₂—Q¹—L+R₃, LR—Q¹—L+R₃ and L+R₂—Q¹—LR₂, wherein Q¹ is a member selected from the same group as for Q except that said Q¹ groups have two points of attachment to L atoms. The compounds also include single or multiply charged inorganic or organic, soluble anions having charges sufficient to balance the charges from any L+ moieties.

In a preferred embodiment of this class of compounds, L in formula II is a phosphorus atom. Particularly preferred ethynyl compounds are of the formulas R₃₋ᵦ'L+C≡C—QL+R₃)ᵦ' (III) and R₃₋ᵦ'P+C≡C—QP+R₃)ᵦ' (IV), wherein b' is an integer from 1 to 3 and R, L and Q are as defined above.

In another preferred embodiment of the invention, at least one R group on the L atom of formula II is a fluoro group. Particularly preferred ethynyl compounds within this class include compounds of the formulas R₂₋ᵦ'FL+C≡C—QP+R₃)ᵦ' (V) and R₂₋ᵦ'FP+C≡C—QP+R₃)ᵦ' (VI), wherein b' is an integer of from 1 to 2 and R, L and Q are as defined above.

Preferably, the compounds of formulas I and II contain from 1 to 3 L+ moieties. In another preferred embodiment, the compounds of I and II contain at least one L+ moiety attached through an ethynyl linkage to an L moiety. In yet another preferred embodiment of the invention involving ethynyl compounds, only one R group attached to an L+ in the compounds of formulas I and II can be a methyl group, unless L of L+ is nitrogen.

The anions balancing the charges from any L+ moieties on the ethynyl compounds of formulas I and II should preferably be non-nucleophilic anions such as carboxylates, phenolates, or halides (the term "halides" as used in this specification and in the attached claims is intended to include F⁻, Cl⁻ or Br⁻ only), more preferably CH₃SO₃⁻, PhSO₃⁻, PhPO₃⁻⁻, Ph₂PO₂⁻, SO₄⁻⁻, PO₄⁻³ or BF₄⁻, and most preferably SbF₆⁻, F₃CSO₃⁻, TaF₆⁻, (SbF₅O₃SCF₃)⁻, (n—C₄H₉)₄B⁻, or Ph₄B⁻. The more polar solvents, such as water, acetic acid, dimethylsulfoxide, CH₃SO₃H, PhSO₃H, F₃CCO₂H or propionic acid, render the anions less nucleophilic, and therefore, even the more nucleophilic of the above anions becomes best suited for use in any desired application. This is especially true of F⁻, Cl⁻ and Br⁻.

The compounds of formulas I and II should contain less than 200 atoms other than hydrogen atoms and halide atoms. Preferably these ethynyl compounds contain less than 100 atoms other than hydrogen and halide, more preferably, they contain less than 75 atoms other than hydrogen and halide, and most preferably, they contain less than 50 such atoms. This count of atoms in the ethynyl compounds does not include those atoms which are part of the anions associated with said compounds.

Suitable compounds of formula I which have been prepared include (1) (diphenylmethylphosphonium)(diphenylphosphino)ethyne methanesulfonate, [Ph₂(CH₃)P⊕C≡CPPh₂⊖O₃SCH₃]; (2)(diphenylmethylphosphonium)(difluorophosphino)ethyne methanesulfonate, [Ph₂(CH₃)P⊕C≡CPF₂ ⊖O₃SCH₃]; (3) ((diethylmethylphosphonium)ethynyl)difluorophosphine trifluoromethanesulfonate, [(C₂H₅)₂(CH₃)P⊕C≡CPF₂⊖O₃SCF₃]; (4) tris((diphenylmethylphosphonium)ethynyl)phosphine tris(methanesulfonate), [(Ph₂(CH₃)P⊕C≡C—)₃P(⊖O₃SCH₃)₃]; and (5) tris(-(diethylmethylphosphonium)ethynyl)phosphine tris(methanesulfonate), [((C₂H₅)₂(CH₃)P⊕C≡C—)₃P(⊖O₃SCH₃)₃]. Other suitable compounds of the formula I containing ethynyl linkages between the heteroatom L and the quaternized heteroatom L+ include (6) (2-(ferrocenyl)ethynyl)((para-methoxy-phenyl)ethynyl)(2-(triethylphosphonium)ethynyl)arsine tetrabutyloranate, [(((C₅H₅)Fe(II)(C₅H₄))C≡C—)(p—CH₃O(C₆H₄—C≡C—)((C₂H₅)₃P⊕C≡C—)As(n—C₄H₉)₄B⊖]; and (7) (2-(trimethylammonium)ethynyl)(ferrocenyl)(2-(triphenylarsonium)ethynyl)phosphine 1,4-bis(tributylboranate)butane, [((CH₃)₃N⊕C≡C—)((C₅H₅)Fe(C₅H₄))(Ph₃⊕ᴬˢC≡C—)-P(n—C₄H₉)₃B⊖CH₂CH₂—)₂].

Suitable non-salt ethynyl compounds included with the scope of formula II which have been prepared include (8) (diphenyl)(ethynyl)phosphine, [Ph₂PC≡CH]; (9) (diethyl)(ethynyl)phosphine, [(C₂H₅)₂PC≡CH]; (10) tris(2-(diphenylphosphino)ethynyl)phosphine, [(Ph₂PC≡C—)₃P]; (11) tris(2-(diethylphosphino)ethynyl)phosphine, [((C₂H₅)₂PC≡C—)₃P]; (12) (diphenylphosphino)(dichlorophosphino)ethyne, [Ph₂PC≡CPCl₂]; (13) (diphenylphosphino)(difluorophosphino)ethyne, [Ph₂PC≡CPF₂]; (14) (diethylphosphino)(dichlorophosphino)ethyne, [(C₂H₅)₂PC≡CPCl₂]; and (15) (diethylphosphino)(difluorophosphino)ethyne, [(C₂H₅)₂PC≡CPF₂]. Other suitable compounds of formula II are (16) bis(2-(pentafluorophenyl)ethynyl)fluorophospine, [((C₆F₅)C≡C—)₂PF]; (17) bis(2-(trifluoromethyl)ethynyl)fluoroarsine, [(CF₃C≡C—)₂AsF]; (18) (2-(bis(-tertiary-butyl)amino)ethynyl)(2-phenoxyethyl)-fluoroarsine, [((((CH₃)₃C)₂N)C≡C—)(C₆H₅OCH₂CH₂—)AsF]; (19) (2-(pentafluorophenyl)ethynyl)(trifluoromethyl)fluorophosphine, [(CF₃)((C₆F₅)C≡C—)PF]; (20) bis(ferrocenyl)(2-(pentafluorophenyl)ethynyl)arsine,

[((C$_5$H$_5$)Fe(C$_5$H$_4$))$_2$((C$_6$F$_5$)C≡C—)As]; (21) tris(2-(trifluoromethyl)ethynyl)phosphine, [(CF$_3$C≡C—)$_3$P]; and (22) tris(2-(pentafluorophenyl)ethynyl)phosphine, [C$_6$F$_5$C≡C—)$_3$P].

Another class of preferred ethynyl compounds are compounds of the formula R$_{2-b}$$^1$F$_b$L—C CR$^1$ (VII). In this formula III, b represents an integer of 1 or 2. Each R$^1$ group is independently selected from the group consisting of an R group and a group Q(J)$_a$, wherein each R group is independently selected from the group consisting of alkyl, alkenyl, alkynyl, aryl, alkoxyalkyl, aryloxyalkyl, alkoxyaryl, aryloxyaryl, ferrocenyl, and fluoro groups, wherein the aryl portions thereof can be substituted with a halogen and the alkyl portions thereof can be substituted with a member selected from halogen and hydroxy groups, provided that the halogens on the alkyl groups are not in an alpha-position with respect to the L atoms unless they are fluoro atoms. Each Q group is independently selected from the group consisting of alkyl, alkenyl, alkynyl, aryl, alkoxyalkyl, aryloxyalkyl, alkoxyaryl, aryloxyaryl, and ferrocenyl, wherein the aryl portions thereof can be substituted with a halogen and the alkyl portions thereof can be substituted with a member selected from halogen and hydroxy groups, wherein said Q groups have a+1 points of attachment to L atoms. The symbol J is selected from the group consisting of LR$_2$, LR—Q$^1$—LR$_2$, LR—Q$^1$—L-R—Q$^1$LR$_2$, L+R$_3$, L+R$_2$—Q$^1$—L+R$_3$, L+R$_2$—Q-$^1$—L+R$_2$—Q$^1$—L+R$_3$, LR—Q$^1$—L+$^R$$_3$ and L+R$_2$—Q$^1$—Q$^1$—LR$_2$ wherein Q$^1$ is a member selected from the same group as for Q except that said Q$^1$ groups have two points of attachment to L atoms and wherein R is defined as hereinabove. These compounds include single or multiply charged inorganic or organic, soluble anions having charges sufficient to balance the charges from any L$^+$ moieties on the compounds. Exemplary of suitable compounds within this class are (23) Bis(2-(pentofluorophenyl)ethynyl)fluorophospine, [((C$_6$F$_5$)C≡C—)$_2$PF]; (24) Bis(2-(trifluoromethyl)ethynyl)fluoroarsine, [(CF$_3$C≡C—)$_2$AsF]; (25) (2-(bis(-tertiarybutyl)amino)ethynyl)(2-phenoxyethyl)fluoroarsine, [(((CH$_3$)$_3$C)$_2$N)C≡C—)(C$_6$H$_5$OCH$_2$CH$_2$—)AsF]; and (26) (2-(pentafluorophenyl)ethynyl)(trifluoromethyl)fluorophosphine, [(CF$_3$)((C$_6$F$_5$)C≡C—)PF].

Another aspect of the present invention relates to a complex VIII comprising a Group VIB, VIIB, VIIIB or IB transition metal in complex association with at least one ligand selected from ethynyl compounds of the formulas I, II, and III, IV, V, VI and VII, wherein the ethynyl compounds contain at least one non-quaternized L atom.

Transition metals for general use in the complexes of formula VIII and the other transition metal complexes described in further detail below include mono-atomic and clusters comprising transition metal atoms. The particular transition metal atom or cluster chosen for use in any particular process depends upon a number of factors, including the conditions of the process being performed and the properties needed for the complexes in the desired process, e.g., certain transition metals are better for use as hydroformylation catalysts than as, say, hydrogenation catalysts. The terminology "transition metal cluster," as used in this specification and the attached claims, is meant to include metal clusters comprising at least one transition metal atom covalently bonded to a member selected from the group consisting of (1) at least one transition metal atom, (2) a group covalently bonded to at least one transition metal atom, which group renders the transition metal atoms thereby joined electronically contiguous, and (3) combinations of (1) and (2) above. Examples of such transition metal clusters (enumerated without specifying the associated ligands thereto) include, e.g., Ru$_3$, Rh$_6$, Fe$_3$, Co$_6$, Mo$_2$, Re$_2$, Pt$_3$, Co$_6$, and Rh$_4$. Suitable atoms for covalently bonding at least two transition metal atoms in the clusters, which atoms render the transition metal atoms thereby joined electronically continguous, include Sn, N, P, H, C, and occasionally O or S.

Among the preferred ligands for use in the complexes of the formula VIII are included the preferred ethynyl compounds described in greater detail above. Thus, exemplary of suitable complexes of formula VIII which were synthesized, include (27) (tris((diphenylmethylphosphonium)ethynyl)phosphine)tetracarbonyliron(O) tris(methanesulfonate), [((Ph$_2$(CH$_3$)P⊕C≡C)$_3$P)Fe(CO)$_4$(CH$_3$SO$_3$⊖)$_3$]; (28) ((diphenylmethylphosphonium) (diphenylphosphino)ethyne)tetracarbonyliron(O) methanesulfonate, [(Ph$_2$(CH$_3$)P⊕C≡CPPh$_2$)—Fe(CO)$_4$CH$_3$SO$_3$⊖]; (29) (tris((diethylmethylphosphonium)ethynyl)-phosphine)-tetracarbonyliron(O) tris(methanesulfonate), [((C$_2$H$_5$)$_2$(CH$_3$)P⊕C≡C—)$_3$(Fe(CO)$_4$(⊖O$_3$SCH$_3$)$_3$]; (30) bis(tris((diethylmethylphosphonium)ethynyl)phosphine)(acetylacetonato)-rhodium(I) hexakis(methanesulfonate), [((C$_2$H$_5$)$_2$(CH$_3$)P⊕C≡C)—$_3$PRh—(C$_5$-H$_7$O$_2$)(CH$_3$SO$_3$⊖)$_6$]; (31) tetrakis(tris((diethylmethylphosphonium)ethynyl)phosphine(platinum(O) dodecakis(methanesulfonate), [((C$_2$H$_5$)$_2$(CH$_3$)P⊕C≡C—)$_3$P)$_4$Pt°(CH$_3$SO$_3$⊖)$_{12}$]; (32) bis(tris(diethylmethylphosphonium)ethynyl)phosphine)dichloroplatinum(II) hexakis(methanesulfonate), [((C$_2$H$_5$)$_2$(CH$_3$)P⊕—C≡C—)$_3$P)$_2$PtCl$_2$ (CH$_3$SO$_3$⊖)$_6$]; (33) tris((diphenylmethylphosphonium)ethynyl)difluorophosphine)carbonylhydridorhodium(I) tris(methanesulfonate), [(Ph$_2$(CH$_3$)P⊕C≡CPF$_2$)$_3$Rh(CO)H-(⊖O$_3$SCH$_3$)$_3$]; (34) tris(((diphenylmethylphosphonium)ethynyl)(difluorophosphine)carbonylhydridoiridium(I) tris(methanesulfonate), [(Ph$_2$(CH$_3$)P⊕C≡CPF$_2$-)$_3$Ir(CO)H(⊖O$_3$SCH$_3$)$_3$]; (35) tris(((diethylmethylphosphonium)ethynyl)difluorophosphine)carbonylhydridorhodium(I) tris(trifluoromethanesulfonate), [(C$_2$H$_5$)$_2$(CH$_3$)P⊕C≡C—PF$_2$)$_3$Rh(CO)H-(⊖O$_3$SCF$_3$)$_3$]; (36) (((diphenylmethylphosphonium)ethynyl)difluorophosphine)tetracarbonyliron(O)methanesulfonate, [(Ph$_2$(CH$_3$)P⊕C≡CPF$_2$)Fe(CO)$_4$-⊖O$_3$SCH$_3$]; (37) (((diethylmethylphosphonium)ethynyl)difluorophosphine)tetracarbonyliron(O) trifluoromethanesulfonate, [(C$_2$H$_5$)$_2$(CH$_3$)P⊕C≡CPF$_2$)Fe(CO)$_4$⊖O$_3$SCH$_3$]; (38) tris(tris((diphenylmethylphosphonium)ethynyl)phosphine)carbonylhydridorhodium(I) nonakis(methanesulfonate), [((Ph$_2$(CH$_3$)P⊕C≡C)—$_3$P)$_3$Rh(CO)H(CH$_3$SO$_3$⊖)$_9$]; and (39) (tris((diphenylmethylphosphonium)ethynyl)-phosphine)tetracarbonyliron(O) tris(methanesulfonate), [((C$_2$H$_5$)$_2$(CH$_3$P⊕C≡C—)$_3$P)Fe(CO)$_4$(⊖O$_3$SCH$_3$)$_3$]. Other suitable complexes of formula VIII are (40) bis(-tris(2-(diphenylphosphino)ethynyl)phenylphosphonium)decacarbonylhexacobalt(O) 1,8-octanedisulfonate, [((Ph$_2$PC≡C—)$_3$P⊕Ph)$_2$Co$_6$(CO)$_{10}$ (—CH$_2$CH$_2$CH$_2$CH$_2$SO$_3$⊖)$_2$]; (41) bis((2-(bis(2-methoxyethyl)phosphino)ethynyl)bis(2-methoxyethyl)-methylphosphonium))tetracarbonylchromium(O) oxalate, [((CH$_3$OCH$_2$CH$_2$)$_2$PC≡CP⊕(CH$_2$C-H$_2$OCH$_3$)$_2$(CH$_3$))$_2$Cr(CO)$_4$C$_2$O$_4$$^{--}$]; (42) ((2-(pentafluorophenyl)ethynyl)difluoroarsine)hexakis(tertiarybutylisocyano)tetranickel(O), [(C$_6$F$_5$C≡C—AsF$_2$-

)Ni$_4$(CNC(CH$_3$)$_3$)$_6$]; (43) ((tertiary-butyl)(2-paramethoxyphenyl)ethynyl)fluorophosphine)nonacarbonyldirhenium(O), [(((CH$_3$)$_3$C)(p—CH$_3$O—(C$_6$H$_4$)C≡C—)PF)Re$_2$(CO)$_9$]; (44) (cyclopentadienyl)(dicarbonyl)(2-(bis(4-hydroxybutyl)methylphosphonium)ethynyl)difluorophosphine)manganese(I) tetrakis(pentafluorophenyl)boranate, [(C$_5$H$_5$)Mn(CO)$_2$(PF$_2$(—C≡C—P⊕(CH$_3$)(CH$_2$CH$_2$CH$_2$OH)$_2$))(C$_6$F$_5$)$_4$B⊖]; (45) (cyclopentadienyl)(carbonyl)(((trifluoromethyl)ethynyl)difluorophosphine)bromoiron-(II), [(C$_5$H$_5$)FeBr(CO)(PF$_2$(—C≡C—CF$_3$))]; and (46) bis(((ferrocenylethynyl)(2-(triethylphosphonium)ethynyl)fluorophosphine)(tri-n-butylphosphine)(triphenylarsine)(triethylphosphite)octacarbonyltriruthenium(O) benzenephosphonate, [(((((C$_5$H$_5$)Fe(II)(C$_5$H$_4$))C≡C—)((C$_2$H$_5$)$_3$P⊕C≡C—)PF)((n—C$_4$H$_9$)$_3$P)(Ph$_3$As)-((C$_2$H$_5$O)$_3$P)Ru$_3$(CO)$_8$)$_2$PhPO$_3$− −]. Other suitable complexes of formula VIII are (40) bis(tris(2-(diphenylphosphino)ethynyl)phenylphosphonium)decacarbonylhexacobalt(O) 1,8-octanedisulfonate, [((Ph$_2$PC≡C—)$_3$P⊕Ph)$_2$Co$_6$(CO)$_{10}$(—CH$_2$CH$_2$CH$_2$CH$_2$SO$_3$⊖)$_2$]; (41) bis((2-(bis(2-methoxyethyl)phosphino)ethynyl)bis(2-methoxyethyl)methylphosphonium))tetracarbonylchromium(O) oxalate, [(((CH$_3$OCH$_2$CH$_2$)$_2$PC≡CP⊕(CH$_2$CH$_2$OCH$_3$)$_2$(CH$_3$))$_2$Cr(CO)$_4$C$_2$O$_4$− −]; (42) ((2-(pentafluorophenyl)ethynyl)difluoroarsine)hexakis(tertiarybutylisocyano)tetranickel(O), [(C$_6$F$_5$C≡C—AsF$_2$)Ni$_4$(CNC(CH$_3$)$_3$)$_6$]; (43) ((tertiarybutyl)(2-(paramethoxyphenyl)ethynyl)fluorophosphine)nonacarbonyldirhenium(O), [(((CH$_3$)$_3$C)(p—CH$_3$O—(C$_6$H$_4$)C≡C—)PF)Re$_2$(CO)$_9$]; (44) (cyclopentadienyl)(dicarbonyl)(2-(bis(4-hydroxybutyl)methylphosphonium)ethynyl)difluorophosphine)manganese(I) tetrakis(pentafluorophenyl)boranate, [(C$_5$H$_5$)Mn(CO)$_2$(PF$_2$(—C≡C—P⊕(CH$_3$)(CH$_2$CH$_2$CH$_2$OH)$_2$))(C$_6$F$_5$)$_4$B⊖]; (45) (cyclopentadienyl)(carbonyl)(((trifluoromethyl)ethynyl)difluorophosphine)-bromoiron(II), [(C$_5$H$_5$)FeBr(CO)(PF$_2$(—C≡C—CF$_3$))]; and (46) bis(((ferrocenylethynyl)(2-(triethylphosphonium)ethynyl)fluorophosphine)(tri-n-butylphosphine)(triphenylarsine)(triethylphosphite)octacarbonyltriruthenium(O) benzenephosphonate, [(((((C$_5$H$_5$)Fe(II)(C$_5$H$_4$))C≡C—)((C$_2$H$_5$)$_3$P⊕C≡C—)PF)((n—C$_4$H$_9$)$_3$P)(Ph$_3$As)-((C$_2$H$_5$O)$_3$P)Ru$_3$(CO)$_8$)$_2$PhPO$_3$− −].

These compounds and complexes of formula I-VIII are useful as solvents and co-solvents and as catalysts in catalytic conversion processes for the conversion of hydrocarbons and carbon monoxide, to desired products, e.g., hydrogenation using as reagents either hydrogen or carbon monoxide and water, dehydrogenation, hydrocarbonylation of olefin, hydrocarbon synthesis, alcohol synthesis, and water-gas disproportionation catalysts (sometimes called water-gas shift. The choice of the particular compound and/or complex depends upon the process desired and the conditions of such process under which it is to be run.

Another aspect of the invention involves ethenyl compounds of the formulas

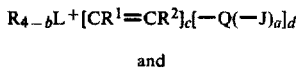

IX and

X

In the compounds of formulas IX and X, the symbols a, b, c, d, a', b', c', d', R, Q, and J are the same as defined above for compounds of formulas I and II. The symbol R$^1$ in the compounds of formulas IX and X represents a member selected from the group consisting of R as defined above and the group Q(J)$_a$ as defined above. The symbol R$^2$ in the compounds of formulas IX and X represents a member selected from the group of R as defined above, J as defined above, Q(J)$_a$ as defined above and F. The compounds of formulas IX and X also contain single or multiply charged inorganic or organic, soluble anions having charges sufficient to balance the charges from any L+ moieties on these compounds.

The preferred compounds of X are those in which L is a phosphorous atom and/or at least one R group on the L atom of formula X is a fluoro group. Exemplary of the preferred ethenyl compounds of this class are of the formulas R$_{3-b'}$L+CR$^1$=CR$^2$L+R$_3$)$_{b'}$ (XI) and R$_{3-b'}$P+CR$^1$=CR$^2$L+R$_3$)$_{b'}$ (XII), wherein b' is an integer of from 1 to 3 and R, R$^1$, R$^2$, L and Q are as defined above. Another group of preferred compounds within this class are those of the formulas FR$_{2-b'}$L+(CR$^1$=CR$^2$—QP+R$_3$)$_{b'}$ (III) and FR$_{2-b'}$P+(CR$^1$=CR$^2$—QP+R$_3$)$_{b'}$ (XIV), wherein b' is an integer of from 1 to 2 and the other symbols used therein have the definitions given above.

(47) (Diphenylphosphino-trans-ethenyl)diphenylmethylphosphonium methanesulfonate, [Ph$_2$P—t—CH=CH—⊕P(CH$_3$)Ph$_2$CH$_3$SO$_3$⊖] was made and is representative of suitable compounds within this class. Other suitable compounds of this class are (48) (Trans-2-(diethylphosphino)propenyl)diethylmethylphosphonium (2-ethylhexyl)tri-secondary-butylboranate, [t—((C$_2$H$_5$)$_2$P)(CH$_3$)C=CHP⊕(C$_2$H$_5$)$_2$(CH$_3$)(s—C$_4$H$_9$)$_3$B⊖(CH$_2$CH(CH$_2$CH$_3$)CH$_2$CH$_2$CH$_2$ CH$_3$)]; (49) ((Diphenylarsino)-cis-ethenyl)diphenylbenzylarsonium pentachlorobenzoate, [Ph$_2$As—cis—CH=CH—As⊕(CH$_2$Ph)Ph$_2$C$_6$Cl$_5$CO$_2$⊖]; and (50) (2-(dicyclohexylphosphino)-2-(dioctylamino)ethenyl)triemethylammonium nonafluorobutanesulfonate, [((c—C$_6$H$_{11}$)$_2$P)((n—C$_8$H$_{17}$)$_2$N)C=CHN⊕(CH$_3$)$_3$n—C$_4$F$_9$SO$_3$⊖]; and other similar materials.

The compounds of formulas IX and X can be used as ligands in complex association with a group VIB, VIIB, VIIIB or IB transition metal atom to form complexes of formula XI. In these complexes, at least one L atom in the compounds of formulas IX and X is a non-quaternized L. The preferred ethenyl-containing ligands for use in these complexes have already been discussed above. Again, the transition metal includes individual atoms and clusters of transition metal atoms as defined above. The ligand in the complexes of formula XV varies depending upon the choice of the reaction, reaction conditions, economics and other similar factors for each instance of use.

(51) (Diphenylphosphino)-trans-ethenyl(diphenylmethylphosphonium)tetracarbonyliron(O), [Ph$_2$⊕P(CH$_3$)—t—CH=CH—PPh$_2$)Fe(CO)$_4$⊖O$_3$SCH$_3$] was prepared and is a typical example of complexes of formula XV. Other suitable members of this class include (52) bis((2,2-bis(triethylphosphonium)ethenyl)diphenylarsine)dichloropalladium(II) bis(-bis(1,4-tri-n-butylboranate)butane)), [((((C$_2$H$_5$)$_3$P⊕)$_2$C=CH(AsPh$_2$))$_2$PdCl$_2$(-(n—C$_4$H$_9$)$_3$B⊖CH$_2$CH$_2$—)$_2$]; (53) (((bis(ferrocenyl)-phosphino)-cis-ethenyl)tris(para-methoxyphenyl)phosphonium)pentacarbonyltungsten(O) trifluoroacetate, [((p—CH$_3$OC$_6$H$_4$)$_3$P⊕—t—CH=CH—P((C$_5$H$_4$ )Fe(II)(C$_5$H$_5$))$_2$)W(CO)$_5$CF$_3$CO$_2$$^\ominus$]; and other similar materials.

In a similar manner for that discussed above with the ethynyl-containing ligands and catalysts, the present ethenyl-containing ligands and catalysts can be employed as solvents and catalysts in conversion reactions for hydrocarbons and carbon monoxide, hydrogenation using H$_2$ or CO plus water, dehydrogenation, hydrocarbonylation of olefins, hydrocarbon synthesis, alcohol synthesis, or water-gas disproportionation. These ethenyl-containing ligands and complexes are in most instances less preferred than the ethynyl ligands and complexes discussed above since the extent of conjugation or electronic contiguity or the extent of the effects on the heteroatoms L through the C$_2$ moiety on the heteroatoms L by the quaternized L+ salts on the opposite end of the C$_2$ moiety are considerably less when the C$_2$ moiety is and ethenyl moiety, rather than an ethynyl moiety. Moreover, the conjugation is 2-dimensional for the ethenyl moiety, while it is 3-dimensional for the ethenyl moiety.

Still another preferred embodiment of the present invention relates to salt ligand complexes of formula XVI comprising a group VIB, VIIB, VIIIB or IB transition metal in complex association with a ligand selected from compounds with structures with the formula

and

In the compound of formula XVII and XVIII, b is an integer of from 1 to 4, while b' is an integer of from 1 to 3. The symbols a and a' represent integers of from 0 to 2. Each L is independently selected from the group consisting of P, As, and N. J is selected from the group consisting of LR$_2$, LR—Q$^1$LR$_2$, LR—Q$^1$—L—R—Q$^1$LR$_2$, L+R$_3$, L+R$_2$—Q$^1$—L+R$_3$, L+R$_2$—Q$^1$—L+R$_2$—Q$^1$—L+R$_3$, LR—Q$^1$—L+R$_3$ and L+R$_2$—Q$^1$—LR$_2$. Each R group is independently selected from the group consisting of alkyl, alkenyl, alkynyl, aryl, alkoxyalkyl, aryloxyalkyl, alkoxyaryl, aryloxyaryl, ferrocenyl, and fluoro groups, wherein the aryl portions thereof can be substituted with a halogen and the alkyl portions thereof can be substituted with a member selected from halogen and hydroxy groups, provided that said halogens on said alkyl groups are not in an alpha-position with respect to said L atom unless they are fluoro atoms. Each Q group is independently selected from the group consisting of alkyl, alkenyl, alkynyl, aryl, alkoxyalkyl, aryloxyalkyl, alkoxyaryl, aryloxyaryl, and ferrocenyl, wherein the aryl portions thereof can be substituted with a halogen and the alkyl portions thereof can be substituted with a member selected from halogen and hydroxy groups and wherein said Q groups have a+1 points of attachment to L atoms. Q$^1$ is a member selected from the group as for Q except that said Q$^1$ groups have two points of attachment to L atoms. The compounds of formulas XVII and XVIII also include single or multiply charged inorganic or organic, soluble anions having charges sufficient to balance the charges from any L+ moieties on the compounds.

In the compounds of formulas XVII and XVIII, L preferably represents phosphorus, both in the L and L+ moieties. The number of L+ moieties in the compounds of I and II is preferably a maximum of 3, more preferably 2 and most preferably 1. The total number of non-hydrogen and non-halide atoms in the compounds of formulas I and II is preferably less than 200, more preferably less than 150 and most preferably less than 75.

Suitable ligands of formulas XVII and XVIII which have been prepared include (54) (2-(diphenylphosphino)ethyl)diphenylmethylphosphonium methanesulfonate, [Ph$_2$P$^\oplus$(CH$_3$)CH$_2$CH$_2$PPh$_2$$^\ominus$O$_3$SCH$_3$]; (55) tris((diphenylmethylphosphonium)ethynyl)phosphine tris(methanesulfonate), [(Ph$_2$(CH$_3$)P$^\oplus$C≡C+$_3$P-($^\ominus$O$_3$SCH$_3$)$_3$]; (56) (2-(diphenylphosphino)ethynyl)diphenylmethylphosphonium methanesulfonate, [Ph$_2$(CH$_3$)P$^\oplus$C≡CPPh$_2$$^\ominus$O$_3$SCH$_3$]; (58) tris((diethylmethylphosphonium)ethynyl)phosphine tris(methanesulfonate), [((C$_2$H$_5$)$_2$(CH$_3$)P$^\oplus$C≡C+$_3$P($^\ominus$O$_3$SCH$_3$)$_3$]; (59) ((difluorophosphino)ethynyl)diphenylmethylphosphonium methanesulfonate, [Ph$_2$(CH$_3$)P$^\oplus$C≡CPF$_2$$^\ominus$O$_3$SCH$_3$]; (60) ((difluorophosphino)ethynyl)diethylmethylphosphonium trifluoromethanesulfonate, [(C$_2$H$_5$)$_2$(CH$_3$)P$^\oplus$C≡C—PF$_2$CF$_3$SO$_3$$^\ominus$]; (62) (2-(diphenylarsino)ethyl)diphenylmethylphosphonium methanesulfonate, [Ph$_2$AsCH$_2$CH$_2$P$^\oplus$(CH$_3$)Ph$_2$$^\ominus$O$_3$SCH$_3$]; (63) 1-(diphenylphosphino+1'-(diphenylmethylphosphonium)ferrocene(II) methanesulfonate, [Ph$_2$P(C$_5$H$_4$)Fe(II)(C$_5$H$_4$)P$^\oplus$(CH$_3$)Ph$_2$$^\ominus$O$_3$SCH$_3$]; (69) bis(2-(diphenylphosphino)ethyl)methylphenylphosphonium methanesulfonate, [(Ph$_2$PCH$_2$CH$_2$)$_2$P$^\oplus$(CH$_3$)PhCH$_3$SO$_3$$^\ominus$]; (73) (2-(diphenylphosphino)ethyl)diphenylmethylphosphonium trifluoromethanesulfonate, [Ph$_2$PCH$_2$CH$_2$P$^\oplus$(CH$_3$)Ph$_2$CF$_3$SO$_3$$^\ominus$]; (75) (6-(diphenylphosphino)hexyl)diphenylmethylphosphonium methanesulfonate, [Ph$_2$P(CH$_2$)$_6$$^\oplus$PPh$_2$CH$_3$SO$_3$$^\ominus$]; (77) 2,2-bis((diphenylphosphino)methylene)(methyl)(diphenylmethylphosphonium)methylene)methane methanesulfonate, [(Ph$_2$PCH$_2$)$_2$(CH$_3$)CCH$_2$$^\oplus$P(CH$_3$)Ph$_2$CH$_3$SO$_3$$^\ominus$]; and (78) (2-(diphenylphosphino)ethyl)(diphenyl)(3-methylbutyl)phosphonium formate, [Ph$_2$PCH$_2$CH$_2$$^\oplus$P(CH$_2$CH$_2$CH(CH$_3$)$_2$)Ph$_2$HCO$_2$$^\ominus$].

These listed ligand materials are typical of the types of ligands used in the formation of the new complex compositions below. Other similar ligands can also be employed in such complexes.

These ligands of formulas XVII and XVIII are useful as solvents and cosolvents for various catalytic conversion processes of hydrocarbons and carbon monoxide. For example, they can be employed as solvents in a catalytic conversion process comprising contacting a reactant selected from hydrocarbon, hydrocarbon precursors, and mixtures of carbon oxides and water with a catalyst so as tocatalytically convert the reactant to the desired product. In such a process the compound of formula XVII and/or XVIII may be used with a cosolvent with which it is miscible, wherein the cosolvent preferably has a pH of greater than about 6.5. Preferably, the compound of formula XVII NS?OE XVIII is the same as the ligand complexed with the catalyst. Examples of such catalytic conversion processes include hydrogenation, dehydrogenation, hydrocarbon synthesis, hydrocarbonylation of olefins or water-gas disproportionation catalysis. In these processes, a catalyst suitable to provide the desired reaction is, of course, employed.

The transition metals of the complexes of formula XVI include single transition metal atoms and clusters thereof as discussed above. The choice of the transition metal, like the choice of ligand, is dependent upon a number of factors including the properties of the ligand attached to the transition metal, the process in which the complex will be used and the conditions of such process, and the costs of the various ligands, metals, catalysts, solvents, etc.

Complexes of formula XVI which were prepared include (79) Tris(2-(diphenylphosphino)ethyl)diphenylmethylphosphonium)carbonylhydridorhodium(I) tris(methanesulfonate), $[(PhP^{\oplus}(CH_3)CH_2CH_2PPh_2)_3Rh(CO)H(^{\ominus}O_3SCH_3)_3]$; (80) (Tris(2-(diphenylmethylphosphonium)ethynyl)phosphine)tetracarbonyliron(O) tris(methanesulfonate), $[(Ph_2(CH_3)P^{\oplus}C\equiv C-_3P)Fe(CO)_4(^{\ominus}O_3SCH_3)_3)]$; (81) (2-diphenylphosphinoethynyl)diphenylmethylphosphonium)tetracarbonyliron(O) methanesulfonate, $[(Ph_2(CH_3)P^{\oplus}C\equiv CPPh_2)Fe(CO)_4{}^{\ominus}O_3SCH_3)]$; (82) (Tris(2-(diethylmethylphosphonium)ethynyl)phosphine)tetracarbonyliron(O) tris(methanesulfonate), $[((C_2H_5)_2(CH_3)P^{\oplus}C\equiv C+_3P)Fe(CO)_4(^{\ominus}O_3SCH_3)_3)]$; (83) Bis(tris(2-(diethylmethylphosphonium)ethynyl)phosphine)(acetylacetato)rhodium(I) hexakis(methanesulfonate), $[((C_2H_5)_2(CH_3)P^{\oplus}C\equiv C+_3P)Rh(C_5H_7O_2)(CH_3SO_3{}^{\ominus})_6]$; (84) Tetrakis(tris(2-(diethylmethylphosphonium)ethynyl)phosphine)platinum(O) dodecakis(methanesulfonate), $[((C_2H_5)_2(CH_3)P^{\oplus}C\equiv C+_3P)_4Pt(O)(^{\ominus}O_3SCH_3)_{12}]$; (85) Bis(tris(2-diethylmethylphosphonium)ethynyl)phosphine)dichloroplatinum(II) hexakis(methanesulfonate), $[((C_2H_5)_2(CH_3)P^{\oplus}C\equiv C+_3P)_2PtCl_2 \cdot (^{\oplus}O_3SCH_3)_6]$; (86) Tris((2-(difluorophosphino)ethynyl)diphenylmethylphosphonium)carbonylhydridorhodium(I) tris(methanesulfonate), $[(Ph_2(CH_3)P^{\oplus}C\equiv CPF_2)_3Rh(CO)H(^{\ominus}O_3SCH_3)_3]$; (87) Tris(2-(difluorophosphino)ethynyl)diethylmethylphosphonium)carbonylhydridorhodium(I) tris(trifluoromethanesulfonate), $[(C_2H_5)_2(CH_3)P^{\oplus}C\equiv C-PF_2)_3Rh(CO)H(CF_3SO_3{}^{\ominus})_3]$; (88) Tris(2-(difluorophosphino)ethynyl)diphenylmethylphosphonium)carbonylhydridoiridium(I) tris(methanesulfonate), $[(Ph_2(CH_3)P^{\oplus}C\equiv CPF_2)Ir(CO)H\ (^{\ominus}O_3SCH_3)_3)]$; (89) Tris(((bis(2-cyanoethyl)phosphinoxy)(di-sec-butoxy)silicoxy)-(tris(sec-butoxy)silicoxy)(((di-sec-butoxy)(bis(2-cyanoethyl)(methyl)phosphoniumoxy)silicoxy)-methylsilane)carbonylhydridorhodium(I) tris(methanesulfonate), $[((((NCCH_2CH_2)_2P-O-)(2-C_4H_9O)_3SiO-)(s-C_4H_9O)_2((NCCH_2CH_2)_2(CH_3)P^{\oplus}O)SiO)SiCH_3)_3Rh(CO)H(^{\ominus}O_3SCH_3)_3]$; (90) Tris(2-(diphenylarsino)ethyl)diphenylmethylphosphonium)carbonylhydridorhodium(I) tris(methanesulfonate), $[(Ph_2AsCH_2CH_2P^{\oplus}(CH_3)Ph_2)_3Rh(CO)H(^{\ominus}O_3SCH_3)_3]$; (91) Tris(1-(diphenylphosphino)-1'-diphenylmethylphosphonium)ferrocene(II)carbonylhydridorhodium(I) tris(methanesulfonate), $[(Ph_2P(C_5H_4)Fe(II)(C_5H_4)P^{\oplus}(CH_3)Ph_2)_3Rh(CO)H(^{\ominus}O_3SCH_3)_3]$; (92) Tris(tris(para-(trimethylammonium)phenyl)phosphine)carbonylhydridorhodium(I)-nonakis(benzenesulfonate), $[(((CH_3)_3N^{\oplus}(p-C_6H_4))_3P)_3Rh(CO)H(PhSO_3{}^{\ominus})_3]$; (93) Tris(2-(diethylphosphino)ethyl)diethylmethylphosphonium)carbonylhydridorhodium(I) tris(methanesulfonate), $[((C_2H_5)_2PCH_2CH_2{}^{\oplus}P(CH_3)(C_2H_5)_2)_3Rh(CO)H(CH_3SO_3{}^{\ominus})_3]$; (94) (Tris(2-(diphenylphosphino)ethyl)(3-methylbutyl)phosphonium)carbonylhydridorhodium(I) methanesulfonate, $[((CH_3)_2CHCH_2CH_2P^{\oplus}(CH_2CH_2PPh_2)_3)Rh(CO)HCH_3SO_3{}^{\ominus}]$; (95) Bis(tris(2-diphenylphosphino)ethyl)methylphosphonium)octacarbonyldihydridohexarhodium bis(methanesulfonate), $[((Ph_2PCH_2CH_2)_3P^{\oplus}CH_3)Rh_6(CO)_8H_2(CH_3SO_3{}^{\ominus})_2]$; (96) (Tris(2-(diphenylphosphino)ethyl)methylphosphonium)octacarbonylhydridorhodium methanesulfonate, $[(Ph_2PCH_2CH_2)_3P^{\oplus}CH_3)Rh_4(CO)_8HCH_3SO_3{}^{\ominus}]$; (97) (Tris(2(diphenylphosphino)ethyl)methylphosphonium)octacarbonylhydridoiridium methanesulfonate, $[((Ph_2PCH_2CH_2)_3P^{\oplus}CH_3)IR_4(CO)_8HCH_3SO_3{}^{\ominus}]$; (98) (Tris-(2(diethylphosphino)ethyl)methylphosphonium)carbonylhydridorhodium(I) trifluoromethanesulfonate, $[((CH_3CH_2)_2PCH_2CH_2)_3P^{\oplus}CH_3)Rh(CO)HCF_3SO_3{}^{\ominus}]$; (99) (Tris(2-(diethylphosphino)ethyl)methylphosphonium)nonacarbonyltetrarhodium(O) methanesulfonate, $[(CH_3P^{\oplus}(CH_2CH_2P(C_2H_5)_2)_3)Rh_4(CO)_9CH_3SO_3{}^{\ominus}]$; (100) Tris(2-(diphenylphosphino)ethyl)diphenylmethylphosphonium)carbonylhydridoidridium(I) tris(methanesulfonate), $[(Ph_2P^{\oplus}(CH_3)CH_2CH_2PPh_2)_3Ir(CO)H(^{\ominus}O_3SCH_3)_3]$; (101) Trans-bis((2-(diphenylphosphino)ethyl)diphenylmethylphosphonium)dichloroplatinum(II) bis(methanesulfonate), $[(t-Ph_2P^{\oplus}(CH_3)C=CHPPh_2)_2PtCl_2 \cdot (^{\ominus}O_3SCH_3)_2]$; (102) Tetrakis(2-(diphenylphosphino)ethyl)diphenylmethylphosphonium)platinum(O) tetrakis(methanesulfonate), $[(Ph_2P^{\oplus}(CH_3)CH_2CH_2PPh_2)_4Pt^{\circ}(^{\ominus}O_3SCH_3)_4]$; (103) Tetrakis((2-(diphenylphosphino)ethyl)diphenylmethylphosphonium)octacarbonyltetrairidium(O) tetrakis(methanesulfonate), $[(Ph_2P^{\oplus}(CH_3)CH_2CH_2PPh_2)_4Ir_4(CO)_8 (^{\ominus}O_3SCH_3)_4]$; (104) ((2-(diphenylphosphino)ethyl)diphenylmethylphosphonium)tetracarbonyliron(O) methanesulfonate, $[(Ph_2P^{\oplus}(CH_3)CH_2CH_2PPh_2)Fe(CO)_4{}^{\ominus}O_3SCH_3]$; (105) Bis((2-(diphenylphosphino)ethyl)diphenylmethylphosphonium)tricarbonyliron(O) bis(methanesulfonate), $[(Ph_2P^{\oplus}(CH_3)CH_2CH_2PPh_2)_2Fe(CO)_3 \cdot (^{\ominus}O_3SCH_3)_2]$; (106) Hexakis((2-(diphenylphosphino)ethyl)diphenylmethylphosphonium)hexacarbonyltriruthenium(O) hexakis(methanesulfonate), $[(Ph_2P^{\oplus}(CH_3)CH_2CH_2PPh_2)_6Ru_3(CO)_6 (CH_3SO_3{}^O-)_6]$; (107) Bis((2-(diphenylphosphino)ethyl)diphenylmethylphosphonium)bis(acetylacetate)ruthenium(II) bis(methanesulfonate), $[(Ph_2P^{\oplus}(CH_3)CH_2CH_2PPh_2)_2Ru(C_5H_2O_2)_2(CH_3SO_3{}^{\ominus})_2]$; (108) Bis((2-(diphenylphosphino)ethyl)diphenylmethylphosphonium)carbonyldichlororuthenium(II) bis(methanesulfonate), $[(Ph_2P^{\oplus}(CH_3)CH_2CH_2PPh_2)_2Ru(CO)Cl_2 \cdot (^{\ominus}O_3SCH_3)_2]$; (109) Bis(triphenylphosphine)((2-(diphenylphosphino)ethyl)diphenyl(3-methylbutyl)phosphonium)carbonylhydridorhodium(I) formate, $[(Ph_3P)_2(Ph_2PCH_2CH_2{}^{\oplus}P(CH_2CH_2CH(CH_3)_2)Ph_2)Rh(CO)HHCO_2{}^{\ominus}]$; (110) Tris((2-(diphenylphosphino)ethyl)(diphenyl)(3-methylbutyl)phosphonium)carbonylhydridorhodium(I) tris(formate), $[(Ph_2PCH_2CH_2{}^{\oplus}P(CH_2CH_2CH(CH_3)_2)Ph_2)_3Rh(CO)H (HCO_2{}^{\ominus})_3]$; and (111) Tris((2-(diphenylphosphino)ethyl)diphenyl)(3-methylbutyl)phosphonium)-carbonylhydridorhodium(I) tribromide, $](Ph_2PCH_2CH_2{}^{\oplus}P(CH_2CH_2CH(CH_3)_2)Ph_2)_3Rh(CO)H (Br^-)_3]$.

The structures and compositions of the listed complexes represent the wide variety of structures and compositions which are suitable for inclusion in these complexes, but other similar materials can also be employed. The complexes of formula XVI are useful as solvents and cosolvents, and as catalysts in catalytic conversion reactions of hydrocarbons and carbon monoxide, such as hydrogenation using, as reagents, $H_2$ or CO plus $H_2O$, dehydrogenation, hydrocarbonylation of olefins, hydrocarbon synthesis, alcohol synthesis and/or water-gas shift disproportionation catalysis.

Yet another aspect of the present invention relates to novel compositions of matter (XIXI) comprising surface tetravalent metal oxide selected from the group consisting of $SiO_2$, $TiO_2$, $ZrO_2$, $HfO_2$, $ThO_2$, $GeO_2$, $SnO_2$ and mixtures thereof and with other metal oxides, and attached to the surface of said tetravalent metal oxide, a coordinating group of a formula selected from $-L^1R_2(XX)$ and $-L^1R_{2-b}+Q+J)_a]_b$ wherein the coordinating group is attached to the tetravalent metal oxide through an oxide linkage. In these new compositions of matter (XIX), each $L^1$ atom is selected from the group consisting of trivalent P and As. The symbol a is an integer of from 1 to 2, while b is an integer of from 1 to 2. Each R is independently selected from the group consisting of alkyl, alkenyl, alkynyl, aryl, alkoxyalkyl, aryloxyalkyl, alkoxy aryl, aryloxyaryl, ferrocenyl, and fluoro groups, wherein the aryl portions thereof can be substituted with a halogen and the alkyl portions thereof can be substituted with halogen groups, provided that said halogens on said alkyl groups are not in an alpha-position with respect to said L atom unless they are fluoro atoms. The symbol Q is a member selected from the group consisting of alkyl, alkenyl, alkynyl, aryl, alkoxyalkyl, aryloxyalkyl, alkoxyaryl, aryloxyaryl, and ferrocenyl, wherein the aryl portions thereof can be substituted with a halogen and the alkyl portions thereof can be substituted with halogen groups and wherein said Q group has $a+1$ points of attachment to L atoms. The atoms J is selected from the group consisting of $LR_2$, $LR-Q^1-LR_2$, $LR-Q^1-LR-Q^1LR_2$, $L+R_3$, $L+R_2-Q^1-L+R_3$, $L+R_2-Q^1-L+R_2-Q^1-L+R_3$, $LR-Q^1-L+R_3$ and $L+R_2-Q^1-LR_2$, wherein $Q^1$ is a member selected from the same group as Q except that said $Q^1$ groups have two points of attachment to L atoms and L is a member independently selected from P, As and N. In these new compositions, L is preferably phosphorous, and the surface tetravalent metal oxide is preferably $SiO_2$ or $TiO_2$, depending on the use to which the novel composition of formula XIX will be put and the conditions to which they will be subjected. The surface tetravalent metal oxide can exist as a coating on a substrate. The surface area of the surface tetravalent metal oxide is preferably greater than 5 square meters per gram, more preferably greater than 50 square meters per gram and most preferably greater than 100 square meters per gram. The average area occupied by each equivalent of L atom should preferably be less than 125 square angstroms per L atom, more preferably less than 100 and most preferably less than 75 square angstroms per equivalent of L atoms wherein the lower limit is the area occupied by a single L atom with a monolayer coverage. These last two statements are true of all the surface tetravalent metal oxide compositions included within the scope of the present invention discussed further below. The R groups on these tetravalent metal oxide compositions and the other tetravalent metal oxide compositions discussed further below should be thermally stable, i.e., they should not include any substituents which would render them thermally unstable such as hydroxy groups because of the methods of preparation of these compounds which involve heating to 200° C. or higher.

Examples of exemplary compounds within this class which were prepared include:
(112) titania-oxydiphenylphosphine, $[TiO_2/Ti-O-Ph/_2]$;
(113) n-titania-oxydiphenylphosphine, $[n-TiO_2/Ti-O-Ph/_2]$; and
(114) silica-oxydiphenylphosphine, $[SiO_2/Si-O-Ph/_2]$. Other suitable compounds within this class are (115) Titania-oxy-bis(2-cyonoethyl)phosphine, $[TiO_2/Ti-O-P(CH_2CH_2CN)_2]$; (116) Silica-oxy-bis(2-cyanoethyl)phosphine, $[SiO_2/Si-O-P(CH_2CH_2CN)_2]$; (117) Titania-oxydiethylphosphine, $[TiO_2/Ti-O-P(CH_2CH_3)_2]$; (118) Thoria-oxy-bis(2-phenylethynyl)phosphine, $[ThO_2/Th-O-P(C\equiv C-Ph)_2]$; (119) Silica-oxy-bis(ferrocenyl)arsine, $[SiO_2/Si-O-As((C_5H_4)Fe(II)(C_5H_5))_2]$; (120) Zirconia-oxybenzylphenylphosphine, $[ZrO_2/Zr-O-P(Ph)(CH_2Ph)]$; (121) Titania-oxydifluorophosphine, $[TiO_2/Ti-O-PF_2]$; (122) n-titania-oxy-(2-bis(diethylmethylphosphonium)ethynyl)phosphine benzenephosphonate, $[n-TiO_2/Ti-O-P(C\equiv CP^{\oplus}(CH_3)(C_2H_5)_2)_2$ $(PhPO_3^{--})]$; (123) n-titania-oxydifluorophosphine, $[n-TiO_2/Ti-OPF_2]$; (124) silica-oxytrifluoromethylfluorophosphine, $[SiO_2/Si-O-PF(CF_3)]$; (125) silica-titania mixed oxide-oxypentafluorophenylfluoroarsine, $[SiO_2-TiO_2/"M"-O-AsF(C_6F_5)]$; and (126) alumina-silica mixed oxide-oxy(2-(tri-n-butyl)silyl)ethyl)fluorophosphine, $[Al_2O_3-"M"O_2/Si-O-PF(CH_2CH_2Si(n-C_4H_9)_3]$; and other similar materials.

The composition of XIX can be used to trap metal, especially transition metals, from liquid or gas streams. They are also useful as intermediate or catalyst precursors in the production of metal complexes as shown below.

Still another aspect of the present invention involves a complex (XX) of a group VIB, VIIB, VIIIB, or IB transition metal in complex association with a ligand of formula XIX as defined above. As with the compounds of formula XIX described above, in the present complexes, the metal oxide comprises a semi-conductor or semi-conductor coated electrode. Preferably, the semi-conductor or semi-conductor coated electrode comprises an n-type $TiO_2$.

These solid ligand materials have as supports materials of low or high surface area in which the surface is a tetravalent metal oxide. The bulk material may or may not be the same material, it can be a metal or a metal oxide or alloy or mixtures of metal oxides which are coated with either the mixture or pure metal oxides such as, titanium dioxide, silicon dioxide, thoreum dioxide, zirconium dioxide, germanium dioxide or hafnium dioxide. It is possible to use tin dioxide as well but this is less preferable. In addition, the support material can be either a conductor, insulator or semiconductor, and for some purposes, it can be partially reduced materials such as n-type titanium in which some of the titanium is reduced to titanium $Ti^{+3}$ to make the titanium dioxide into a semiconductor. The three examples actually employed were silicon dioxide or silica ($SiO_2$), titanium dioxide or titania ($TiO_2$), and ($n-TiO_2$) or semiconductor titania in which some of the titanium has been reduced. In the discussions and formulas that follow only the metal part of the support such as titanium Ti or silicon Si will be shown as the formula in showing the reactions with and structures with the materials on the surfaces.

The primary linkage which characterizes the material is a structure with an M—O—L linkage. The L atoms are specifically either phosphorus or arsenic in their trivalent states and in which the other two substituents on the phosphorus or arsenic are organic substituents, that is, they are bonded through a carbon to the atom L. The primary group thus attached on the support for the formation of such a ligand can be diphenylphosphineoxy group. Thus, preferred ligand structures are $TiO_2/$-$Ti/Ti$—O—$PR_2$, $SiO_2/Si$—O—$PR_2$ and $n$—$TiO_2/Ti$—O—$PR_2$.

These materials act as if there were phosphine ligands even though they have an oxygen attached to the phosphorus, making them somewhat like esters of phosphonic acids. However, because there is a metal M attached on the other side of the oxygen, they cannot be called normal esters, nor can they be thought of as ester type materials because they do not act like phosphate materials in their reactions with metals and the formation of catalysts. A useful way in which these materials are very like phosphines rather than phosphinic acid esters is that they can still form salts such in a very similar manner to phosphonium salts. In the salt preparations they are reacted with a quaternizing addition compound such as methylmethane sulphonate, methyltrifluoromethanesulfonate, methylbromide, methylbenzenesulfonate or other similar materials form simple addition compounds to form a quaternized phosphonium salt with the appropriate anion such as methanesulfonate, bromide, benzenesulfonate, triflouromethanesulfonate, etc. Furthermore, such ligands and salts of such ligands do not decompose in the same fashion that other organoxy-phosphorus derivatives. This is because the rearrangements involving oxygen migration allowing the phosphorus/oxygen double bond linkages are essentially blocked by the electron withdrawing nature of the metals on the other side of the oxygen in the case of the present types of ligands and salts. Thus, for all intents and purposes, including naming purposes, it is quite appropriate to consider these materials as pseudo-phosphines, pseudo-arsines, pseudo-phosphonium salts and pseudo arsonium salts. Within these materials, it is preferable to have the atom L be a phosphorus, rather than arsenic.

The preferences expressed with respect to the compound of formula XIX above includes some of the preferred ligands for the complexes of formula XX. Other preferred ligands for these complexes include compounds wherein at least one R group is a fluoro group. In another preferred embodiment, the density of ligand functions on the surface is such that the L atoms are sufficiently close together on the surface to allow ligand functions attached to the surface of the tetravalent metal oxide to function as a chelating ligand, wherein two or more L atoms can attach to a given metal atom or cluster thereof.

Preferred metals for use in the complexes of formula XX include ruthenium, rhodium, iron and platinum. Transition metal clusters as defined above can also be employed. The preference for any of these transition metals is dependent upon the use to which the complex material is to be put. For instance, for photo reactions using the complexes of formula XX, the transition metal is most preferably ruthenium. A preferred complex of this last class useful for photo reactions is n—$TiO_2$ supported bis(Titania-oxydiphenylphosphine)bis(2,2'-bipyridine)dichlororuthenium(II). This is a cationic material and will change valence during the courses of such reactions so for obvious reasons the appropriate anions are necessary to counterbalance the charge. The associated anions can and typically do change even during the course of the reactions because of the change in valence state of the transition metal.

Thus, in one application of the complexes of formula XX, they can be used in a photoreaction process comprising contacting the complex in the presence of water with visible or ultraviolet light to thereby decompose the water. Preferably, such a process is conducted at a pH of between about 5 and about 95. The preferred metal is ruthenium complexed by at least two bipyridinic ligands and preferably complexed by a chelating ligand attached to a semiconducting support. The attachment is preferably by way of covalent attachments or linkages which render the metal complex electronically contiguous with the semiconductor electrode. The said semiconductor electrode or semiconductor coated conducting electrode to which the metal complex is linked is preferably connected to a counterelectrode by way of an external circuit through which an electrical load may be applied in order to extract work from the catalyzed photoreaction of water. Alternatively, the obverse situation may be utilized to generate hydrogen, $H_2$, at an electrode by the photoreaction of water either directly or with the application of a small bias voltage. In any case, the net energy available and usable as hydrogen or electrical energy is considerably larger than without such a photoreaction.

Suitable complexes of formula XX which were prepared include (127) (Titania-oxydiphenylphosphine)iron(O)tetracarbonyl, [$TiO_2/Ti$—O—($Ph_2$)P—Fe(CO)$_4$]; (128) Silica-bis(oxydiphenylphosphine)rhodium(I)acetylacetonate, [$SiO_2/$(Si—O—($Ph_2$)P)$_2$—Rh(I)($C_5H_7O_2$)]; (129) Titania-bis(oxydiphenylphosphine)tetrarhodium(O)decacarbonyl, [$TiO_2/$(Ti—O—$Ph_2$P)$_2$—Rh$_4$(O)(CO)$_{10}$]; (130) Titania-bis(oxydiphenylphosphine)triruthenium(O)decacarbonyl, [$TiO_2/$(Ti—O—(Ph)$_2$P)$_2$—Ru$_3$(CO)$_{10}$] (131) Titania-bis(oxydiphenylphosphine)dichloroplatinum (II), [$TiO_2/$(Ti—O—$Ph_2$)P)$_2$—cis—PtCl$_2$]; (132) Titania-(oxydiphenylphosphine)carbonylrhodium(I)acetylacetonate, [$TiO_2/Ti$—O—(Ph)$_2$—P—Rh(CO)($C_5H_2O_2$)]; (133) Titania-(oxydiphenylphosphine)dicarbonyldichlororuthenium(II), [$TiO_2/Ti$—O—(Ph)$_2$P—Ru(CO)$_2$Cl$_2$]; and (134) n-titania-bis(oxydiphenylphosphine)bis(2,2$^1$-bi-pyridine)dichlororuthenium(II), [n—$TiO_2/$(Ti—O—(Ph)$_2$P)$_2$(H$_5$NC$_5$—C$_5$NH$_5$)$_2$RuCl$_2$]. Other suitable complexes within this class are (134) Thoria-bis(oxy-bis(pentafluorophenyl)phosphine)-tricarbonylhydridorhenium(I), [$ThO_2/$(Th—O—(F$_5$C$_6$)$_2$P)$_2$—Re(CO)$_3$H]; (135) Zirconia-(oxybis(2-cyanomethyl)phosphine)pentacarbonylmolybdenum(O), [$ZrO_2/Zr$—O—(NCCH$_2$CH$_2$)$_2$P—Mo(CO)$_5$]; (136) Germanium-(oxydiethylphosphine)copper(I) trifluoromethanesulfonate, [$GeO_2/$Ge—O—(C$_2$H$_5$)$_2$P—Cu$^{\oplus}$ $^{\ominus}$O$_3$SCF$_3$]; (137) Titania-(oxydiferrocenylarsine)tricarbonylnickel(O), [$TiO_2/Ti$—O—((C$_5$H$_5$)Fe(II)((C$_5$H$_4$))$_2$As—Ni(CO)$_3$]; (138) Titania-bis(oxydifluorophosphine)tetradecacarbonylhexarhodium(O), [$TiO_2/$(Ti—O—PF$_3$)$_2$Rh$_6$(CO)$_{14}$]; (139) Titania-bis(oxy(bispentafluorophenyl)fluorophosphine)dicarbonylnickel(O), [$TiO_2/$(Ti—O—PF(C$_6$F$_5$)$_2$)$_2$Ni(CO)$_2$]; and other similar materials.

The complexes of formula XX can also be used as catalysts in conversion reactions of hydrocarbons and carbon monoxide, e.g. in reactions such as hydrogenation with hydrogen or CO plus water, dehydrogenation, hydrocarbonylation of olefins, hydrocarbon synthesis, alcohol synthesis, water-gas disproportionation or photo reactions as discussed above, for example, photo reactions of water, including photoelectrolysis of water for the purpose of producing electrical energy or the production of hydrogen, $H_2$.

Still another embodiment of the present invention is directed to a composition of matter (XXI) comprising surface tetravalent metal oxide selected from the group consisting of $SiO_2$, $TiO_2$, $ZrO_2$, $HfO_2$, $ThO_2$, $GeO_2$, $SnO_2$ and mixtures thereof, said metal oxide having a salt group bonded to said metal through an oxide linkage wherein said salt group is a member selected from the formulas $—O—^+L^1R_3$ (XXII) and $—O—^+L^1R_{3-b}[Q(-J)_a]_b$ (XXIII). Each L atom is selected from the group consisting of trivalent P and As. The symbol a is an integer of from 1 to 2, while b is an integer of from 1 to 3. Each R is independently selected from the group consisting of alkyl, alkenyl, alkynyl, aryl, alkoxyalkyl, aryloxyalkyl, alkoxy aryl, aryloxyaryl, ferrocenyl, and fluoro groups, wherein the aryl portions thereof can be substituted with a halogen and the alkyl portions thereof can be substituted with halogen groups, with the proviso that said halogens on said alkyl groups are not in an alpha-position with respect to said L atom unless they are fluoro atoms. The symbol Q is a member selected from the group consisting of alkyl, alkenyl, alkynyl, aryl, alkoxyalkyl, aryloxyalkyl, alkoxyaryl, aryloxyaryl, and ferrocenyl, wherein the aryl portions thereof can be substituted with a halogen and the alkyl portions thereof can be substituted with halogen groups and wherein said Q group has a+1 points of attachment to L atoms. The symbol J is selected from the group consisting of $LR_2$, $LR—Q^1—LR_2$, $LR—Q^1—L-R—Q^1LR_2$, $L^+R_3$, $L^+R_2—Q^1—L^{+R_3}$, $L^+R_2—Q^1—L^+R_2—Q^1—L^+R_3$, $LR—Q^1—L^+R_3$ and $L^+R_2—Q^1—LR_2$, wherein Q is selected from the same group as for Q except that said $Q^1$ groups contain two points of attachment to the atoms, and wherein L is independently selected from P, As and N. The compounds of formula XXI also include single or multiply charged inorganic or organic, soluble anions having charges sufficient to balance the charges from any $L^+$ moieties.

In a preferred embodiment of the compounds of formula XXI the salt group is $—O—^+L^1R_3$. Another preferred embodiment comprises a compound of XXI wherein the $+L^1$ moiety attached to the metal oxide through the oxide linkage contains at least one, more preferably two, and most preferably three aryl groups, preferably phenyl groups. Another preferred group of compounds of formula XXI are those in which a methyl or ethyl group attached to the $+L^1$ bonded to the metal oxide through the oxide linkage.

The discussion above with respect to the concentration of L atoms of the metal oxide surface likewise applies here. This concentration is greater than 0.2 of a milliequivalents per gram when the titania has a surface area of 123 square meters per gram. That concentration is barely sufficient for chelation.

The anions associated with these compounds of formula XXI can be essentially any anion balancing the charges of the $L^+$ moieties. Unreactive anions, i.e., anions that are not strongly oxidizing or reducing; are most preferable. In some instances, such as when the materials are to be used as intermediates for subsequent exchange of anions for another use, it is preferred to have small, relatively polar anions such as chloride, bromide, sulfate, methanesulfonate, $BF^-$, $SbF_6^-$ and other similar anions.

The solid materials of the type in which there is an M—O—L type bond attaching the "phosphine" can be quaternized as mentioned previously by reaction with quaternizing addition compounds. Such quaternizing addition compounds cannot be acids; they must be ester or halide materials of the sorts that are used to make conventional quaternized salt compounds. Typical examples of quaternizing addition compounds include methyl methanesulfonate, methyl trifluoromethanesulfonate, methylbenzenesulfonate, methyl bromide, benzyl bromide, benzyl methanesulfonate, benzyl benzenesulfonate, butyl methanesulfonate, etc. Such quaternizations are accomplished just as if the material being quaternized were a true phosphine rather than the pseudo-phosphine or pseudo-arsine type materials which are actually being quaternized. Thus, in this instance the oxygen moiety on the phosphorus are oxygen need not be considered different than the substituents in which carbon is attached directly to the phosphorus or arsenic. These quaternized solid materials then become very much equivalent to the other organic and inorganic ion exchange materials in which the solid material has large numbers of quaternary salt functionalities allowing anions to be exchanged at will. The best quaternization agents typically are those which are very reactive and form very stable quaternary salts. Thus, the methyl and phenyl derivatives are particularly useful in this regard. Other reagents that are particularly useful for quaternizing the pseudo-phosphines and pseudo-arsines include the oxonium and sulfonium salts. Thus, trimethyloxonium and triethyloxonium tetrafluoroborate, triphenyloxonium fluoroborate, trimethylsulphonium and triphenylsulphonium chlorides are all useful in this regard. In fact, the oxonium and sulfonium salts were the reagents of choice used in the preparation of these species of formula XXI.

Suitable compounds of formula XXI, which were synthesized, include (140) Silica-oxytriphenylphosphonium tetrafluoroborate, [$SiO_2/Si—O—P^{\oplus}\phi_3$ $^{\ominus}BF_4$]; (141) Silica-oxydiphenylmethylphosphonium tetrafluoroborate, [$SiO_2/Si—O—P^{\oplus}\phi_2(CH_3)$ $^{\ominus}BF_4$]; (141a) Silica-oxydiphenylethylphosphonium tetrafluoroborate, [$SiO_2/Si—O—P^{\oplus}\phi_2(C_2H_5)$ $^{\ominus}BF_4$]; (142) Titania-oxytriphenylphosphonium tetrafluoroborate, [$TiO_2/Ti—O—P^{\oplus}\phi_3$ $^{\ominus}BF_4$]; (143) n-Titania-oxytriphenylphosphonium chloride, [$n—TiO_2/Ti—O—^{\oplus}P\phi_3$ $^{\ominus}Cl$]; and (144) Titania-oxydiphenylmethylphosphonium methanesulfonate, [$TiO_2/Ti—O—^{\oplus}P\phi_2(CH_3)CH_3SO_3^{\ominus}$]. Other suitable compounds within this class are (145) Silica-oxydiphenylmethylphosphonium methanesulfonate [$SiO_2/Si—O—P^{\oplus}(CH_3)Ph_2$ $^{\ominus}O_3SCH_3$]; (146) Titania-oxydibenzylphenylarsonium tetrafluoroborate, [$TiO_2/Ti—O—As^{\oplus}(CH_2Ph)_2Ph$ $^{\ominus}BF_4$]; (147) Thoria-bis(oxytri-n-butylphosphonium) sulfate, [$ThO_2/(Th—O—^{\oplus}P(n—C_4H_9)_3)_2 SO_4^{\ominus}$]; (148) Silica-oxytrimethylphosphonium triethyl-2-ethylhexylboranate, [$SiO_2/Si—O—^{\oplus}P(CH_3)_3$ $(C_2H_5)_3B^{\ominus}(CH_2CH(CH_2CH_3)CH_2CH_2CH_2CH_3)$]; (149) Zirconia-oxytriphenylphosphonium hexafluoroantimonate, [$ZrO_2/Zr—O—^{\oplus}PPh_3$ $^{\ominus}SbF_6$]; (150) n-Titania-oxybenzyldiphenylphosphonium bromide, [$n—TiO_2/Ti—O—^{\oplus}P(Ph_2)(CH_2Ph)$ $Br^{\ominus}$]; (151)

Titania-bis(oxy(bis(2-chloroethyl)phosphonium)-μ-(para-xylylene) bis(tetrabromoaluminate), [TiO$_2$/(Ti—O—(ClCH$_2$CH$_2$)$_2$P$^\oplus$)$_2$(—CH$_2$—p—(C$_6$H$_4$)—CH$_2$—)($^-$AlBr$_4$)$_2$)]; and other similar materials.

The compounds of the formula XXI are useful as ion exchange materials for cleaning of liquid streams, recovery of anionic materials from liquid streams, and ion exchangeable supports for exchangeable ligand materials and catalysts made from such materials as discussed below.

The compounds of the formula XXI above are useful in essentially similar, but oppositely changed roles and uses to the cation exchangeable solid materials discussed above. Thus, these materials can be the preferred choices for many uses in which the cation exchangeable materials are unsuitable or in which less than optimal performance or stability is obtained.

The present invention also involves ion-exchanged ligand compositions in which an anion of formulas X$^-$QLR$_2^1$ (XXII) or R$_3^1$B$^-$QLR$_2^1$ is ion-exchanged onto a solid cationic support comprising a composition of formula XXI as defined above. In formula XXII, each R$^1$ group independently represents a member selected from an R group and a group Q(J)$_a$, wherein said R group is selected from alkyl, alkenyl, alkynyl, aryl, alkoxyalkyl, aryloxyalkyl, alkoxy aryl, aryloxyaryl, ferrocenyl, and fluoro groups, wherein the aryl portions thereof can be substituted with a halogen and the alkyl portions thereof can be substituted with a member selected from halogen and hydroxy groups, provided that said halogens on said alkyl groups are not in an alpha position with respect to said L atom unless they are fluoro atoms. The symbol Q is a member selected from the group consisting of alkyl, alkenyl, alkynyl, aryl, alkoxyalkyl, aryloxyalkyl, alkoxyaryl, aryloxyaryl, and ferrocenyl, wherein the aryl portions thereof can be substituted with a halogen and the alkyl portions thereof can be substituted with a member selected from halogen and hydroxy groups, wherein said Q group has a+1 points of attachment to L atoms, and wherein said Q group can be substituted with —X$^-$ groups, said X and R being as defined above. The symbol J is selected from the group consisting of LR$_2$, LRQLR$_2$ and LRQLRQLR$_2$, wherein L, Q and R are as defined above.

In the foranate anions of the formula XXIII, X$^-$ is a member selected from —CO$_2^-$, —SO$_3^-$, —SO$_2^-$, —PO$_3^{--}$, and —RPO$_2^-$. Each R$^1$ group independently represents a member selected from an R group and a group Q$^1$(J$^2$)$_a$, wherein said R and a symbols being as defined in the formula of XXII. The symbol Q$^2$ represents a group Q as defined above except that Q$^2$ can be substituted with —X$^-$ or —A$^-$R$_3$ groups, wherein X, A, and R are as defined above. The symbol J$^2$ represents a member selected from the group consisting of LR$_2$, LRQ$^1$LR$_2$ and LRQLRQLR$_2$, wherein L, Q$^2$ and R are as defined above for formula XXII. Preferably, L represents phosphorus in the foranate anionic quaternary salt ligands of formula XXIII. Also, X is preferably selected from the group consisting of CO$_2^-$ and SO$_3^-$. These quaternary anionic salt ligand can also be supported by deposition onto a solid Lewis acid support such as SiO$_2$, TiO$_2$, Al$_2$O$_3$, mixtures, etc.

These ion-exchanged ligand compositions of formulas XXII and XXIII can be and were formed by conventional ion-exchange techniques. Moreover, they can form complexes with transition metal atoms of Groups VIB, VIIB, VIIIB and IB. These ion-exchange ligand compositions have been found to be suitable for use in various catalytic conversion processes, and particularly in catalytic conversions of hydrocarbons and carbon monoxide, especially those employing a mixture of carbon monoxide and water. They are particularly useful in those situations where there is a desirability to attach the ligand functional group L to the anion moiety rather than to the cationic moiety.

Suitable complexes for these catalytic reactions, which have been prepared, include (152) titania-tris(oxy(triphenylphosphonium)) tris(4-(diphenylphosphino)butanesulfonate)carbonylhydridorhodium(I), [TiO$_2$/(Ti—O—P$^\oplus$Ph$_3$)$_3$(Ph$_2$PCH$_2$CH$_2$CH$_2$CH$_2$SO$_3^\ominus$)$_3$Rh-(CO)H]; (153) silica-oxy(triphenylphosphonium) ((2-(di-n-butylphosphino)ethyl)-para-benzoate)tetracarbonyliron(O), [SiO$_2$/Si—O—P$^\oplus$Ph$_3$($^\ominus$O$_2$C-(p—C$_6$H$_4$)CH$_2$CH$_2$P(n—C$_4$H$_9$)$_2$)Fe(CO)$_4$]; (154) n-titania-bis(oxy)(methyldiphenylphosphonium)) bis(4-(diphenylphosphino)butanesulfonate)bis(acetylacetate)-ruthenium(II) mixed with (1:1)n-titania-bis(oxy(methyldiphenylphosphonium)) bis(4-(diphenylphosphino)-butanesulfonate)dicarbonylnickel(O), and (155) n-titania/(Ti—O—P$^\oplus$(CH$_3$)Ph$_2$)$_2$($^\ominus$SCH$_2$CH$_2$CH$_2$CH$_2$PPh$_2$)$_2$Ni(-CO)$_2$.

Still another aspect of the present invention involves silicate cluster compositions of matter of the formula

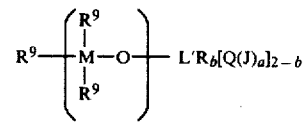

XXIV

In this formula, the symbol a is an integer of from 0 to 2, while b is an integer of from 0 to 2. Each L is selected from the group consisting of trivalent P and As. Each R group is independently selected from the group consisting of alkyl, alkenyl, alkynyl, aryl, alkoxyalkyl, aryloxyalkyl, alkoxyaryl, aryloxyaryl, ferrocenyl, and fluoro groups, provided that (1) the aryl portions of said R group can be substituted with a halogen and the alkyl portions of said R group can be substituted with a member selected from halogen and hydroxy groups, (2) said halogens on said alkyl groups are not in an alpha-position with respect to said L atom unless they are fluoro atoms; and (3) the fluoro groups are not attached directly to the M atom. Each Q group is independently selected from the group consisting of alkyl, alkenyl, alkynyl, aryl, alkoxyalkyl, aryloxyalkyl, alkoxyaryl, aryloxyaryl, and ferrocenyl, wherein the aryl portions thereof can be substituted with a halogen and the alkyl portions thereof can be substituted with a member selected from halogen and hydroxy groups. The symbol J is selected from the group consisting of LR$_2$, LR—Q$^1$—LR$_2$, LR—Q$^1$—LR—Q$^1$LR$_2$, L$^+$R$_3$, L$^+$R$_2$—Q$^1$—L$^+$R$_3$, L$^+$R$_2$—Q$^1$—L$^+$R$_2$—Q$^1$—L$^+$R$_3$, LR—Q$^1$—L$^+$R$_3$ and L$^+$R$_2$—Q$^1$—LR$_2$, wherein Q$^1$ is a member selected from the same group as Q except that said Q$^1$ groups have two points of attachment to L atoms, and wherein L is selected from P, A, and N. M is a member selected from the group consisting of Si, Ti and mixtures thereof. R$^9$ is a member selected from the group consisting of an R group, an OR group, a group Q(J)$_a$, a group OQ(J)$_a$, and an

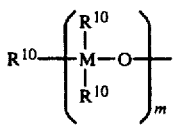

group wherein $R^{10}$ is a member selected from R, OR, $Q(J)_a$ and $OQ(J)_a$, wherein R, Q, J and a are as defined above for formula XXIV, and wherein m is an integer of from 0 to about 200. These compounds also include single or multiply charged inorganic or organic, soluble anions having charges sufficient to balance any charges from $L^+$ moieties contained in the compounds.

In these compounds M preferably comprises Si. In one preferred group of compounds within this class M comprises Si and $R^9$ comprises

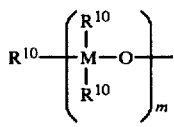

wherein m is an integer of from 1 to 5. Another group of preferred compounds within this class include those in which at least one $R^9$ comprises

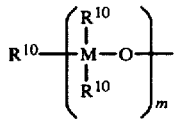

wherein m is independently chosen for each $R^9$ as an integer from 1 to 5. In this last group of compounds, each of the $R^9$ and $R^{10}$ preferably independently are selected from R and/or OR groups. Still another preferred group of compounds within this class are those in which L comprises trivalent P, while another group of preferred compounds are those in which the L group comprises trivalent phosphorus and the J group comprises a quatarenized $L^+$ group. In general, the silicate cluster compounds of formula XXIV preferably contain less than 250 non-hydrogen and non-halide atoms, more preferably they contain less than 150 such atoms, and most preferably they contain less than 100 of such atoms.

With the silicate cluster ligands and for that matter to a somewhat lesser extent with all the ligands discussed in the present application, the proper choice of ligands for a desired catalyst and catalyst application includes consideration of the steric bulk of the ligand which might be used. It should be pointed out that the silicone or titanium "cluster" type materials discussed above are among the exceptionally bulky ligands, especially when the total number of non-hydrogen and non-halide atoms is in the upper portion of the range discussed above, and also in instances when m in the range of from 3, 4, 5 and likewise when the various R groups (such as R, $R^1$, $R^2$, $R^9$ groups etc. are bulky groups.

The compounds of formula XXIV can be prepared by a novel process in accordance with the present invention. In this novel process an addition reaction is performed between a compound selected from $R_2P$—$Pr_2$, $R_2POH$, $R_2PH$ and $R_2PH$ on the one hand, and a material having M—O—C or M—O—M bonds on the other. The materials containing M—O—M bonds also include the surface tetravalent metal oxides discussed above. This reaction is conducted at a temperature sufficient to cause the desired reaction between said compounds and said material to thereby form the compound of formula XXIV, wherein the R groups are as defined above, provided that the R groups are stable at the reaction temperature. For example, the R groups cannot contain alkyl hydroxyl groups. It should be noted that the compounds of the formulas $R_2P$—OH and $R_2PH$ are in equilibrium with each other, the equilibrium depending upon the temperature of the reaction and the nature of the R substituents. Typically, the temperature of this preparation reaction is in the range of from 200° to 400° C., depending upon the nature of the R substituents and the nature of the substrate material having M—O—C or M—O—M bonds. In this reaction, the preferred M atoms are silicone or titanium, although where the starting material is a solid metal oxide surface, the metals can also be hathium, zirconium, thorium, germanium, and sometimes tin. The conditions of this reaction also depend upon how thoroughly the solid metal oxide surface is dried and calcined, also upon the surface area of the metal oxide and upon the phase or physical structure of the metal oxide reactant, that is, on the extent of surface defects which are the most reactive sites.

Suitable compounds of formula XXIV which have been prepared include (153) bis(tri-sec-butoxysilicoxy)(-(diphenylphosphinoxy)di-sec-butoxysilicoxy)methylsilane [((s—C$_4$H$_9$—O—)$_3$SiO)$_2$Si(CH$_3$)—(O—Si—(O—s—C$_4$H$_9$)$_2$—(O—PPh$_2$)); (154) bis(tri-sec-butoxysilicoxy)(bis(2-cyanoethyl)phosphinoxydi-sec-butoxysilicoxy)methylsilane [((s—C$_4$H$_9$—O—)$_3$Si—O—)$_2$-Si(CH$_3$)—(O—Si—O—s—C$_4$H$_9$)$_2$-(⊖O—P(CH$_2$CH$_2$CN)$_2$))]; (155) bis(bis(2-cyanoethyl)-phosphinoxydi-sec-butoxysilicoxy)(tri-sec-butoxy silicoxy)methylsilane [((NCCH$_2$CH$_2$)$_2$P—O—)(s—C$_4$-H$_9$—O—)$_2$Si—O—)$_2$((s—C$_4$H$_9$—O—)$_3$Si-—O—)SiCH$_3$]; and (156) (bis(2-cyanoethyl)phosphinoxydi-sec-butoxysilicoxy)((bis-(2-cyanoethyl)methyloxyphosphonium)di-sec-butoxysilicoxy)(tri-sec-butoxysilicoxy)methylsilane methanesulfonate [((NCCH$_2$CH$_2$)$_2$(CH$_3$)P⊕—O—Si—(O—s—C$_4$H$_9$)$_2$—O—)Si(CH$_3$)(O—Si—O—s—C$_4$H$_9$)-$_2$(O—P(CH$_2$CH$_2$CH)$_2$))⊖O$_3$SCH$_3$].

Other suitable compounds within this class are (157) (tributylsilicoxy)diphenylphosphine, [(n—C$_4$H$_9$)$_3$Si—o—PPh$_2$]; (158) (bis(3-(trimethylammonium)butyl)-(bis(2-methoxyethyl)silicoxy) (bis(4-hydroxybutyl)-phosphine)(4-sulfonato-n-butyl)(tri-n-butyl)boranate, [((CH$_3$N⊕CH(CH$_3$)CH$_2$CH$_2$Si(CH$_3$OCH$_2$CH$_2$)O—P(-CH$_2$CH$_2$CH$_2$CH$_2$OH)$_2$⊖O$_3$SCH$_2$CH$_2$CH$_2$B⊖ (n—C$_4$H$_9$)$_3$]; (159) (2-((trimethylsilicoxy)fluoro-phosphino)ethynyl)triphenylarsonium hexafluorosilicate, [((CH$_3$)$_3$SiO—PF(—C C—As⊕Ph$_3$))$_2$SiF$_6$⊖]; (160) tris(trifluoromethylsilicoxy)phosphine, [((CF$_3$)$_3$Si-O—)$_3$P]; (161) tris(tris(2,4,6-trimethylphenoxy)silicoxytitanoxymethylfluorophosphine, [((2,4,6-(CH$_3$)$_3$(C$_6$H$_2$)—O—)$_3$Si—O—)$_3$Ti—O—PF(CH$_3$)]; and similar materials.

Another aspect of the present invention comprises the use of the compounds of formula XXIV as ligands in complexes of formula XXV of Group VIB, VIIB, VIIIB, or IB transition metals. Again, the metals used in these complexes include the individual transition metals and transition metal clusters as discussed above. The preferred ligands for use in these complexes include the preferred compounds of formula XXIV as discussed above. Considerable numbers of complexes of formula XXIV have been prepared. Other suitable complexes of formula XXV are (164) tris((tributylsilicoxy)diphenylphosphine)carbonylhydridorhodium(I), [((n—C$_4$H$_9$)$_3$Si—O—PPh$_2$)$_3$Rh(CO)H]; (165) tris(((trihexylsilicoxy)-2-ethyl)((dimethyl)silicoxy)diphenylphosphine)carbonylhydridorhodium(I), [((n—C$_6$H$_{13}$)$_3$Si—O—Si(CH$_3$)$_2$—O—PPh$_2$)Rh(CO)H]; (166) tris(((-tributylsilicoxy)-2-ethyl)((dibutyl)silicoxy)diphenylphosphine)carbonylhydridoiridium(I), [((n—C$_4$H$_9$)$_3$Si—O—Si(n—C$_4$H$_9$)$_2$—O—PPh$_2$)Ir(CO)H]; (167) trimethylsilyloxy(pentadeca(dimethylsilicoxy))diphenylphosphine)tricarbonylnickel(O); (168) [((CH$_3$)$_3$Si—(O—Si(CH$_3$))—O—PPh$_2$)Ni(CO)$_3$]; (169) tris((tris(phenoxy)titanium)oxy-bis(ferrocenyl)arsine)nonacarbonyltetrarhodium(O) [((Ph—O—)$_3$Ti—O—As((C$_5$H$_4$)Fe(II)(C$_5$H$_5$))$_2$)$_3$Rh$_4$(CO)$_9$]; (170) (((tri-n-butylphosphoniumoxy)(diphenoxy)silicoxy)(di-para-methoxyphenoxytitanoxy)(diphenoxysilicoxy)dibutylphosphine)(tri-n-butylphosphine)bis(acetylacetato)ruthenium(II) triethyl-2-ethylhexylboranate, [((n—C$_4$H$_9$)$_3$-P$^\ominus$—O—Si (Ph—O—)$_2$—0—Ti(CH$_3$O(p—C$_6$H$_4$)—O—)$_2$—O—Si (Ph—O—)$_2$—O—P(n—C$_4$H$_9$)$_2$)(-(n—C$_4$H$_9$)$_3$P) Ru(C$_5$H$_7$O$_2$)$_2$(C$_2$H$_5$)$_3$B$^\ominus$(CH$_2$CH(C$_2$H$_5$)CH$_2$ CH$_2$CH$_2$CH$_3$)]; (171) tris(((1-((2-(tri-n-butylsilyl)ethy)(p-tolyl)phosphino)-1'-ferrocenyl)methynyl)(dimethylsilicoxytriethylphosphonium)(dimethylsilicoxy)diphenylphosphine)carboxylhydridorhodium(I) tetrachloroaluminate, [((((n—C$_4$H$_9$)$_3$SiCH$_2$CH$_2$)(p—CH$_3$C$_6$H$_4$)P)((C$_5$H$_4$)Fe(II)(C$_5$H$_4$))CH(Si(CH$_3$)$_2$O—$^\oplus$P(C$_2$H$_5$)$_3$)(Si(CH$_3$)$_2$OPPh$_2$))$_3$Rh(CO)H$^\ominus$AlCl$_4$]; (172) tris((2-(tri-n-pentylsilyl)ethyl)(ferrocenyl)(para-tolyl)phosphine)carbonylhydridorhodium(I), [(((n—C$_5$H$_{11}$)$_3$SiCH$_2$CH$_2$—)((C$_5$H$_5$Fe(II)(C$_5$H$_4$))(CH$_3$(p—C$_6$H$_4$))P)$_3$Rh(CO)H]; and similar materials.

The compounds of formula XXIV and the transition metal complexes of formula XXV as described above can be used as solvents and cosolvents, and as catalysts in conversion reactions of hydrocarbons and carbon monoxide, such as hydrogenation with H$_2$ or with carbon monoxide and water, dehydrogenation, hydrocarbonylation of olefins, hydrocarbon synthesis, alcohol synthesis and water-gas disproportionation. Because of the bulkiness of the ligands in the complexes of formula XXV, fewer of the ligands fit around the transition metal atom or cluster thereof which is to be used as a catalyst, thus allowing coordination positions on the transition metal atom or cluster to be available for reactions with substrates and reagents. Alternatively, such bulky ligands arrange themselves on opposite sides of the transition metal atom or cluster thereof due to their large size, thus allowing different coordination positions to be open for reaction with substrate and reagent materials than with less bulky ligands or chelating ligands. Another alternative way in which the bulky ligands of complexes of formula XXV affect the structures of the catalyst materials and therefore the reactions in which they are used is that such bulky ligands, particularly when two or more of such ligands are present on the metal or cluster of metals, often modify the coordination geometry of the ligands on the complex because of the rearrangements of the ligands within the coordination sphere caused by their bulkiness. Examples of this change in coordination geometry include changes from octahedral to tetragonal bipyramidal, square planar to tetragonal square, and pyramidal to trigonal bipyramidal. Bulky ligands such as the compound of formula XXIV would typically occupy the axial positions in trigonal biprymidal and tetragonal bipyramidal coordination geometries, whereas less bulky ligands would occupy or could occupy the equatorial positions either solely or as well as the axial positions in such coordination geometries. Likewise, lowest chelating ligands would occupy solely equatorial positions or equatorial positions in combination with axial positions, but in almost no case could it occupy both axial positions.

A cobalt reaction product catalyst mixture (XXVII) comprises another embodiment of the present invention. This reaction product catalyst mixture comprises cobalt metal, ligand, in the presence of H$_2$ and CO at a temperature and pressure sufficient to obtain a catalyst capable of catalyzing a hydrocarbonylation reaction, wherein said ligand comprises a compound of the formula R$_{3-b}$L'$\$_b$ (XXVI). In the ligand compounds of XXVI, L' is selected from the group consisting of trivalent P and As. Each R is independently selected from the group consisting of alkyl, alkenyl, alkynyl, aryl, alkoxyalkyl, aryloxyalkyl, alkoxyaryl, aryloxyaryl, and ferrocenyl groups, wherein the aryl portions thereof can be substituted with a halogen and the alkyl portions thereof can be substituted with a member selected from halogen and hydroxy groups, with the proviso that said halogens on said alkyl groups are not in an alpha-position with respect to said L atom unless they are fluoro atoms. Each $ group is independently selected from the group consisting of F and —C≡CR$^1$, wherein R$^1$ is selected from the group consisting of R, L+R$_3$, Q$^1$L+R$_3$, L+R$_2$Q$^1$L+R$_3$, L+R$_2$Q$^1$L+R$_2$Q$^1$L+R$_3$, wherein R is defined as and Q$^1$ is selected from a group consisting of alkyl, alkenyl, alkynyl, aryl, alkoxyalkyl, aryloxyalkyl, alkoxyaryl, aryloxyaryl and ferrocenyl, wherein the aryl portions thereof can be substituted with a halogen and the alkyl portions thereof can be substituted with a member selected from halogen and hydroxy groups. The symbol b in formula XXVI is an integer of from 1 to 3.

The ligands of formula XXVI as defined above can also be used in another embodiment of the invention comprising a complex (XXVIII) containing a transition metal selected from the group consisting of chromium, molybdenum, tungsten, manganese, rhenium, iron, ruthernium, osmium, nickel palladium, platinum, copper, silver and gold and mixtures of such metals along with the ligand of the formula XXVI.

These same ligands of formula XXVI can also be used in another embodiment of the present invention comprising a complex XXIX containing transition metal selected from Rh$^{+1}$ and Ir$^{+1}$ along with at least one ligand having the formula XXVI as defined above. The Rh$^{+1}$ and Ir$^{+1}$ transition metals in these complexes can be present either alone or in combination with rhodium or iridium atoms of other valencies or for that matter with other transition metals of varying valencies and other non-transition metals such as in transition metal atom clusters as defined above. In the complexes of formula XXVI, the transition metal preferably comprises Rh$^{+1}$ or Rh in combination with other rhodium atoms in metal clusters containing 4 or 6 rhodium atoms. The tetrarhodium cluster is particularly preferred.

In the complexes of formulas XXVII, XXVIII, and XXIX, the preferred ligands are selected independently from the group consisting of the compounds of formula XXVI in which there is only one non-quaternized L atom, compounds of the formula XXVI containing only one non-quaternized L atom and compounds of the formula $R_{3-b}^1LF$ wherein b is an integer of 1, 2 or 3; L is selected from the group consisting of P and As; $R^1$ is selected from the group consisting of R, $L+R_3$, $Q^1L+R_3$, $L+R_2Q^1L+R_3$, $L+R_2Q^1L+R_2Q^1L+^R_3$, wherein R is selected from the group consisting of alkyl, alkenyl, aryl, alkoxyalkyl, aryloxyalkyl, alkoxyaryl, aryloxyaryl, and ferrocenyl groups, wherein the aryl portions thereof can be substituted with a halogen and the alkyl portions thereof can be substituted with a member selected from halogen and hydroxy groups, with the proviso that said halogens on said alkyl groups are not in an alpha-position with respect to said L atom unless they are fluoro atoms and wherein $Q^1$ is selected from a group consisting of alkyl, alkenyl, alkynyl, aryl, alkoxyalkyl, aryloxyalkyl, alkoxyaryl, aryloxyaryl and ferrocenyl, wherein the aryl portions thereof can be substituted with a halogen and the alkyl portions thereof can be substituted with a member selected from halogen and and hydroxy groups.

Suitable complexes of formulas XXVIII and XXIX, which were prepared, include:

(173) bis(bis(ferrocenyl)fluorophosphine)tricarbonylion(O),

[(((C$_5$H$_5$)Fe(C$_5$H$_4$))$_2$PF)$_2$Fe(CO)$_3$];

(174) ((2-difluorophosphino)ethynyl)diphenylmethylphosphonium)tetracarbonyliron(O)methanesulfonate,

[($\emptyset$(CH$_3$)P$^\oplus$C≡CPF$_2$)Fe(CO)$_4$CH$_3$SO$_3$$^\ominus$];

(175) ((2-(difluorophosphino)ethynyl)diethylmethylphosphonium)tetracarbonyliron(O)trifluoromethanesulfonate,

[((C$_2$H$_5$)$_2$(CH$_3$)P$^\oplus$C≡CPF$_2$)Fe(CO)$_4$(F$_3$CSO$_3$$^\ominus$)];

(176) bis(pentafluorophenyldifluorophosphine)dicarbonylnickel(O),

[((C$_6$F$_5$)PF$_2$)$_2$Ni(CO)$_2$];

(177) tris(di-tertiary-butylfluorophosphine)tricarbonylmolybdenum,

[(((CH$_3$)$_3$C)$_2$PF)$_3$Mo(CO)$_3$]; and (178) tris(pentaphenylethynyldifluorophosphine)monocarbonyl triruthenium(O),

[(C$_6$F$_5$C≡C—PF$_2$)$_3$Ru$_3$(CO)$_9$].

The present invention also includes an anion quaternary salt ligands of the formula $R_3^1B^-QLR_2^1$ XXXII and Group VIB, VIIB, VIIIB and IB transition metal complexes thereof, wherein each L atom is selected from the group consisting of trivalent P, As and N; each R is independently selected from the group consisting of alkyl, alkenyl, alkynyl, aryl, alkoxyalkyl, aryloxyalkyl, alkoxy aryl, aryloxyaryl, ferrocenyl, and fluoro groups, wherein the aryl portions thereof can be substituted with a halogen and the alkyl portions thereof can be substituted with a member selected from halogen and hydroxy groups, with the proviso that said halogens on said alkyl groups are not in an alpha position with respect to said L atom unless they are fluoro atoms; Q is a member selected from the group consisting of alkyl, alkenyl, alkynyl, aryl, alkoxyalkyl, aryloxyalkyl, alkoxyaryl, aryloxyaryl, and ferrocenyl, wherein the aryl portions thereof can be substituted with a halogen and the alkyl portions thereof can be substituted with a member selected from halogen and hydroxy groups and wherein said Q group has a+1 points of attachment to L atoms; J is selected from the group consisting of LR$_2$, LR—Q$^1$—LR$_2$, LR—Q$^1$—LR—Q$^1$LR$_2$, L+R$_3$, L+R$_2$—Q$^1$—L+R$_3$, L+R$_2$—Q$^1$—L+R$_2$—Q$^1$—L+R$_3$, LR—Q$^1$—L+R$_3$ and L+R$_2$—Q$^1$—LR$_2$, wherein Q$^1$ is selected from the same group as for Q except that Q$^1$ groups have two points of attachment to L atoms; and single or multiply charged inorganic or organic, non-solid anions of J having charges sufficient to balance the charges from the L+ moieties X$^-$ is a member selected from —CO$_2$—, —SO$_3$—, —SO$_2$—, —PO$_3$=, and —R-PO$_2$—; each R$^1$ group independently represents a member selected from an R group and a group Q$^1$(J$^2$)$_a$, wherein said R is as defined above; and a is an integer of from 1 to 2; Q$^2$ represents a group Q as defined above except that Q$^2$ can be substituted with —X— or —A$^-$R$_3$ groups, wherein X, A, and R are as defined above; and J$^2$ represents a member selected from the group consisting of LR, LRQ$^1$LR$_2$ and LRQLRQLR$_2$, wherein L, Q$^2$ and R are as defined above.

Examples of suitable ligands of formula XXXII, which were prepared, include tetramethylammonium A-(diphenylphosphino)butanesulfonate,

[(CH$_3$)$_4$N$^\oplus$ $^\ominus$O$_3$SCH$_2$CH$_2$CH$_2$CH$_2$P$\emptyset_2$]; and the analogous sodium salt thereof;

tetramethylammonium (2-(di-n-butylphosphino)ethyl)-para-benzoate,

[(CH$_3$)$_4$N$^\oplus$ (n—C$_4$H$_9$)$_2$PCH$_2$CH$_2$(p—C$_6$H$_4$)CO$_2$$^\ominus$]; and the analogous sodium salt thereof; and tetramethylammonium (4-(diethylphosphino)butyl)triethylboronate,

[(CH$_3$)$_4$N$^\oplus$ (C$_2$H$_5$)$_3$B$^\ominus$CH$_2$CH$_2$CH$_2$CH$_2$P(n—C$_4$H$_9$)$_2$], and the analogous lithium salt thereof.

BEST MODE OF CARRYING OUT THE INVENTION

The preparation of all the salt ligands within the present invention were done by techniques well-known in the art, with minor modifications to suit the particular solubilities, volatilities and stoichiometries involved. Specifically, the salts were made by contacting the "ligand" material tobe quaternized with a quaternizing addition compound such as methylmethansulfonate, dimethylsulfate, methylburylnide, methylbenzenesulfonate, trimethyloxoniumfluoroburate, triphenyloxoniumfluoroburate, triethyloxoniumfluoroburate, triphenylsulfoniumchloride, octylbromide, 2-exylhexylbromide, methyliodide and other similar sorts of compounds with the appropriate structure for the desired added materials to form the quaternary phosphoniumarsonium, etc. compound. Such materials were added under conditions of very high dilution reaction which is a well-known art and evolving somewhat over the past century. The quaternizing addition compound was added in appropriate stoichiometric amount to turn part or a fraction of the ligand moieties of an otherwise chelating ligand into a partial salt ligand compound. This means that, for example, one of two phosphine functionalities in an otherwise diphosphine chelating ligand is turned into a phosphonium salt leaving the other one present as the free phosphine still usable as a ligand moiety.

Most of the quaternizing addition compounds and most of the chelating ligands which were starting materials to form the salt ligands were obtained directly from commercial sources. Others were made by very standard techniques from precursors which were available. In such a situation, small amounts of non-salt chelating ligands were present in the reaction product mixture. These di-salt non-ligand materials are present due to the inevitable statistical distributions except that the reactions being run in very high dilution and with such other precautions helped to minimize the undesired reaction products. Normal recrystalization techniques were followed wherein typically between four and six recrystallizations were sufficient to purify the salt ligand compounds. The elemental analyses and other analyses showed these materials and others to be pure enough within experimental error to be usable for the formation of pure metal complexes for use as catalysts. Other proofs of structure which were obtained on selected examples amidst the wide variety of salt ligand materials formed were acid titrations of the amount of remaining ligand and infrared data confirmation of structures. Very detailed information was obtained on the purity of the materials by such means, and whether or not the functional groups were present, etc. In all cases in which materials were made, they were purified and accepted as the desired materials only after elemental analysis, for all the elements obtainable, e.g., oxygen is not available, were within experimental error of the calculated theoretical composition.

A typical reaction to produce a partial salt ligand, is the reaction of bis(diphenylphosphino)ethane or diphos in an 0.25 mole quantity dissolved in 2.5 liters of purified toluene in a 5 liter flask in which the solvent was refluxing at approximately 112° to 115° C. under an $N_2$ atmosphere. High-speed stirring was used. An 0.25 mole quantity of methyl methanesulfonate was dissolved in 1 liter of purified toluene and the solution was added drop-wise over six days at the rate of one drop per 5 seconds, with an extra 2½ days of refluxing after the final addition to make sure that the reaction was complete. The work-up of the material which typically coated the sides of the flask was quite standard and was done in a manner to prevent contamination by $H_2O$, air, etc. After dissolution and recrystallization four times, the reaction gave 0.20 moles of the product (2-(diphenylphosphino)ethyl)methyldiphenylphosphonium methanesulfonate.

Obviously, this preparation is a typical simple addition reaction run at a high dilution to form the quaternary salt. This type of reaction was basically a production-scale run on a high dilution system. This type of reaction was done many many times to make the various partial salt materials used as salt ligands herein. The preparations of the non-ligand salt solvents were even easier and still very conventional. They involved the complete quaternization of the ligand functionalities by the use of the stoichiometric plus ten percent amounts of quarternizing addition reagents. The starting ligands were typically only single ligands, although a few chelating materials were converted to polyquaternary salts. The other difference in the reactons was that high dilution conditions were not necessary and the apparatus was thus much simpler.

The fluorophosphine ligands typically were made, likewise, by a conventional substitution reaction in which fluoride was substituted for chloride on the ligand material or precursor. Chlorine-containing materials, that is, dichlorophosphines and chloroorganic phosphines were obtained commercially or were made from readily available starting materials in conventional manner. Substitution of fluorine for chlorine again was a typical substitution reaction in which the chloroorganophosphine was passed across a fluorine salt, potassiumfluorosulfite, a common fluorine exchange medium, at high temperatures, typically between 100° and 200° C., depending on the volitility of the compound in question and its reactivity. The fluorine product materials were much more volatile and were removed by distillation from the insoluble and nonvolatile potassium chloride. The volatile $SO_2$ byproduct was easily separable from the organofluorophosphine during distillation. Distillation and recrystalization were used for purifications depending upon the volatility of the materials. Elemental analyses again were used as primary proof of structure, in combination with sequential reactions and elemental analyses of the subsequent reaction products as well.

The acetylenic phosphines were made by simply taking the sodium acetylide salts formed by reaction of commercially available acetylenes with sodamide with byproduct ammonia eliminated. The sodium acetylide was then reacted with the phosphorus halides to make the appropriate phosphine precursors which was then used to make the quaternized salt in the manner described above. These materials as well, like all of the others, were submitted for elemental analysis after purification for proof of structure.

Elemental analysis on all available elements, especially metals phosphorus, carbon, hydrogen, nitrogen, arsenic, were performed on all of the metal complexes and agreed with an experimental error with the calculated theoretical elemental compositions. Consequently, since the materials were simply substitution reactions and very little could happen which was unexpected in such simple substitution reactions where a ligand is substituted for, in general, carbon monoxide. This was considered quite sufficient proof of structure for the metal complexes. In addition, on a selected number of materials, infrared analysis were used to confirm many portions of the structures which were susceptible to Ir or infrared analytical techniques. In particular, carbonyl stretching frequencies and similar such peaks were confirmed in the appropriate regions for a significant number of the metal complexes which were synthesized. The results of the many tests of hydrogenation using hydrogen as a reagent were uniformally excellent and essentially complete during the running of the wide variety of metal complexes. A selected number of some 25 approximate metal catalyst systems were tested for their hydrogenation capabilities in the test of hydrogenation of cyclohexene with the metal catalyst chosen from all of the major groupings of catalyst synthesized herein, and the results were uniformly good with hydrogenation at the standard conditions at room temperature and 50 PSig hydrogen pressure in dimethylether for 1 hour. In all cases, 97 to 100% cyclohexane product as shown by the GC. Typically 3 cycles were run in each test in order to provide evidence that the catalyst was not being irreversibly changed during the course of such reaction.

Dehydrogenation reactions were typically run on the same catalyst as the hydrogenation reactions and the conditions shown above were the dihydrogenation tests. In all of these cases, absolutely all of these cases, the amount of benzene formed at 50 pounds pressure of inert gas nitrogen simply by contacting the 1,4-cyclohexadiene with catalyst quantities of about 0.01 to 0.02 mmoles per 5 grams of substrate cyclohexadienes. In the poorest case, the amount of benzene yield was over 98%. Likewise, 3 cycles typically showed the same thing and even in those cases where it was as low as 98.93% in the first cycle, it got better to the point where after on the third cycle it was 100.0%. Thus, it is fairly obvious that this broad range of catalysts all have very good dihydrogenation capability, just as they all have broadly hydrogenation capability.

The formation of the metal complexes from the metal salts or other metal complexes is also quite straight-forward and well-known in the art. Simple exchange reactions, particularly when a volatile ligand is involved, such as carbon monoxide, which it almost is in this sort of reaction since the starting material metal complexes are 0 valent or low valent metal salts in almost all circumstances. This means that simply the stoichiometrically desired amount of ligand or ligands is added to the mixture in a solvent which is typically toluene, ethyl alcohol, tetrahydrofuran, dimethyl ether or mixtures thereof. The materials were heated until the carbon monoxide was driven off and the material reached equilibrium, typically done at solvent reflux or slightly above, or if the solvent, like dimethylether boils very low, the reaction is done in an autoclave and heated up to 80° to 100° C. The other solvents typically reflux between 60° and 110° C. Reactions are very mild for these conversions. In some cases, in order to preserve the identity of the catalyst or convert to the appropriate material, synthesis gas in 1:1 ratio, that is, hydrogen and carbon monoxide in 1:1 ratio was typically applied as an atmosphere at approximately 250 to 300 psig in order to help convert the appropriate materials to their carbonylhydrides. Syngas pressure was applied in essentially all the cases with cobalt, rhodium, and iridium during the formation of the catalysts. The other metals did not need such application, and such complex preparations were made in an inert atmosphere $N_2$ rather than under syngas atmosphere.

A catalyst which was useful in hydrocarbonylation, hydrogenation, dehydrogenation, alcohol and hydrocarbon-synthesis and water-gas shift was made using $Rh_2(CH_3CO_2)_4$ as the rhodium starting material and the ligands (2-(diphenylphosphino)ethyl)methyldiphenylphosphonium methanesulfonate. Stoichiometric amounts of 3 equivalents of the ligand with 1 equivalent of rhodium were used to make the product which had a general formula of $L_3Rh(CO)H$. In this case, 13.6 mmoles of the ligand were reacted with 2.3 mmoles of the dirhodium specie or 4.55 mmoles of rhodium metal with a result that after recrystalization three times to purify the product, 3.4 mmoles of product was obtained. The reaction was run under carbon monoxide $H_2$ syngas pressure of 304 psig with syngas in 1:1 ratio with THF solvent under nitrogen in a Teflon-lined autoclave at 80° C. for 17 hours. After distilling off the solvent, all the work-up and recrystalizations were also done under nitrogen. This typical method is known in the art for the preparation of this type of metal complex. Likewise, the other metal complexes in the present invention were prepared by similar well-known techniques in the art with minor modifications depending on the metals and the ligands.

Hydrogenation tests in which $H_2$ hydrogen was the reducing agent were done in the Teflon-lined autoclave at 50 psig hydrogen pressure using cyclohexene as the substrate. The solvent was 200 milliliters of dimethyl ether and 5.0 grams of cyclohexene feed was treated in the autoclave using 0.1 millimoles of catalyst, either in slurry form if the catalyst was a solid or in solution if it were a soluble catalyst. The reaction was run at 25° C. ambient temperature and with a time per cycle of one hour. At the end of a cycle the ether and the ether solvent and the hydrocarbon product and starting materials were distilled off; the ether fractionated away from the resulting materials which were then injected into a GC and analyzed for cyclohexane percentage relative to cyclohexene starting material. The catalyst remained in the autoclave reactor vessel to which was then added an additional aliquot of solvent and an additional aliquot of feed material the cyclohexene for another cycle. Typically three cycles were run in each test in order to determine whether the catalyst was being irreversably changed during the course of such reactions. In a small proportion of cases the solvent was changed as noted.

The dehydrogenation test cases were run in a manner very similar to the hydrogenation test cases. However, the feed material was 1,4-cyclohexadiene and the gas above the solution was nitrogen $N_2$ pressurized to 50 psig in order to keep the low boiling solvent dimethylether as a liquid. One hour cycles were again used and 5 gram aliquots of feed as well. The reactions were run at 25° C. and the pressure within the reactor was allowed to increase as it would with the evolution of the hydrogen. Work-up of the reaction products was identical and the GC results were used to determine percentage of benzene relative to other cyclohexane, cyclohexene, cyclohexadiene products. Again the amount of catalyst used was in the 0.01 to 0.02 millimole range and typically three cycles were run in order to determine whether any irreversible damage or changes were occurring to the catalysts or catalyst mixture. In every case most of the reaction for the dehydrogenation evidently occurred almost immediately upon addition of the feed substrate material to the reaction mixture. The reaction was so fast that it could be watched in terms of the rise of pressure immediately upon addition of the cyclohexadiene. This despite the fact that the reaction was basically endothermic and a decrease in temperature was occurring simultaneously with the production of hydrogen.

The testing for the reduction using carbon monoxide and water was typically done in a completely different mode. Specifically again, it was done in this 500 cc capacity Teflon-lined autoclave, but if the solvent was then 1 to 1 by volume, dimethyl ether to water, 200 milliliters total, reaction was done at 80° C. and under a CO pressure of 355 psig. Again, the same quantity of catalyst was used; same catalyst range of 0.01 to 0.02 millimoles of catalyst and 5 gram charges of cyclohexene were used as the substrate. The cycle lengths were 2½ hrs. long unless otherwise noted. In these reactions typically only part of the cyclohexene was reduced, somewhere around 50% under the reaction conditions and in addition a certain amount of cyclohexane aldehyde was formed as an oxynation product. Typically the oxynation product was in the 2 or 3% range. Such catalysts, because there was water present and so forth, were also tested for hydrogenation using $H_2$ for comparison and were also checked for water gas shift reaction and dehydrogenation also.

The conditions under which the cobalt oxynation reactions or cobalt hydrocarbonylation reactions were run are considerably modified from the conditions under which actual commercial units run, partially due to the limitations of the apparatus and partially due to the fact that the reactions were run in a Teflon-lined autoclave which had certain constraints on pressure and temperature. Thus, the hydrocarbonylation reactions were run under much milder conditions than the hydrocarbonylation reactions are run in normal commercial cobalt catalyzed systems. But because the reactions were run under very mild conditions where hardly any reaction occurs with plain cobalt catalysts it tended to point out the improvements quite readily that certain of the phosphine ligand addition materials can do in order to promote the reaction at milder conditions, that is lower temperatures and lower pressures than commercial units at. And furthermore because these reactions were run under such mild conditions where very little of the starting material olefin was reacted the overall differences in normal to iso aldehyde yields also are indicative of what would happen under the much more severe conditions under which commercial units would run. Thus, it should be noted that the results reported herein are all internally consistent and comparable to one another. Those materials which work better at lower conditions would also work better at the higher conditions but are that much better and more useful and desirable in that respect also. Thus, when hydrocarbonylation tests were done using no additional phosphine, essentially no reaction was accomplished over the course of the normal run, and after one hour at 225° C. only 4/10% of the propylene had reacted. Still at 225° C. the addition of triphenylphosphine gave essentially the same results, whereas lowering the temperature to 165° C. and adding tributyl phosphine allowed the reaction to go to the level of 0.85% of the propylene being reacted in the same time span. With phenyldifluorophosphine as the addition material, 9.4% of the propylene starting material reacted and with diphenylfluoro phosphine, 5.08% of the propylene reacted; and finally with the difluorophosphinoethynyl diethylmethylphosphonium trifluoromethanesulfonate phosphine being used, 10.11% of the propylene had reacted in one run at 165° C. and 23.63% of the propylene had reacted in another cycle at 200° C. Thus, quite clearly, the more of the fluorines or pseudo-fluorines that are on the phosphine that is used as the ligand, the better the catalyst in terms of the rate of catalysis. Thus, these materials make the reaction go at less severe conditions. Furthermore, the improvement in normal to iso ratio of product butraldehydes improves in the same direction with a similar correlation: the more fluoro or pseudo-fluoro substituents on the phosphine, the higher the normal to iso ratio.

The testing for water gas shift typically was done in a similar part of system to that for testing with CO/water reduction of olefins where some gas was pressured into the reactor at approximately 355 psig at 80° C. using a solvent in a 1 to 1 ratio of 200 milliliters split between dimethylether and water. Again, 0.1 to 0.2 millimoles of catalyst were used and the cycle lengths were not of concern because samples of gas were taken in a flow through system after specific times. The reactions were done at atmospheric pressure and 100° C. as well at the temperature of boiling water and samples were taken at specific times for GC analysis and mass spec analysis. Typical times taken for samples were at the start of the reaction essentially 0 minutes, generally approximately 30 minute time and at an hour and two hours and an overnight sample, typically on the order of 16 to 17 hours after the start of the run in order to determine whether there was any catalyst degradation during the period of time or improvement.

The testing for hydrogenation of olefins using water and carbon monoxide was done on relatively few catalysts because of the demonstrable ubiquity of hydrogenation capability as demonstrated by the hydrogenation catalysis results and dehydrogenation catalysis results as reported above. In a typical reaction, 0.05 mmoles catalysts which was, for example, a bis ligand platinum dichloride. The ligand was tris((diethylmethylphosphonium)ethynylphosphine) trismethanesulfonate which obviously was changed during the course of the reaction, because the resulting catalyst which was removed from the reactor showed, by Ir analysis, a platinum-carbonyl bonding. The reaction was done in a dimethylether-water solvent 1:1 by volume of 200 ml of salt-solvent at 80° C. in the Teflon-lined autoclave with stirring, and with 2½ hour cycles. The catalyst was dissolved in the solvent and work-up was by distillation of the solvent and product from the catalyst and analysis tests by GC. In the first cycle of such a test, there was 49.2% cyclohexane and 46.8% remaining starting material cyclohexene, with 4% other materials primarily cyclohexanealdehyde. The second cycle yielded 54.9% cyclohexane with correspondingly lower amounts of the other two materials, and the third cycle produced 55.1% cyclohexane with correspondingly lower amounts of the other materials. So obviously the catalyst was improving in its efficiency over the course of the reaction for the reduction of cyclohexene to cyclohexane. Its activity was quite evident even though the reaction was considerably slower than a hydrogenation using hydrogen itself. The infrared analysis of the catalyst showed that the carbon carbon triple bonds still existed after such a reaction so that the platinum was not hydrogenating its own ligands. At higher temperature in the fourth cycle at 120° C. 92.2% cyclohexane was obtained.

A large number of tests were made for testing hydroformylation of olefins, particularly of propene with the improved yields of the desired normal butraldehyde and minimizing the amount of iso butyraldehyde. Likewise, the goal of running each hydroformylation reactions at less severe conditions, that is at lower temperatures and pressures and higher feed rates of syngas and propylene feed materials was also realized. Advantage was taken of the zero volatility of the salt ligands and of the resulting complexes and salt solvents. Continuous hydroformylation reaction process which was demonstrated in outline, at least, because all products were distilled from the reaction mixture solvent-catalyst mixture before analysis. This test is typical of a continuous reaction run batchwise, the only way possible in this laboratory to approximate continuous commercial processing. The catalyst and solvent systems stayed in situ unless the light ethers were used as solvents.

INDUSTRIAL APPLICABILITY

The compositions and processes of the present invention can be used in catalytic conversion of hydrocarbons and carbon monoxide in the reactions, hydrogenation, dehydrogenation, hydrocarbonylation of olefins, hydrocarbon synthesis, alcohol synthesis and water-gas disproportionation.

What is claimed is:

1. A complex comprising a carbonyl ligand, a transition metal selected from the group consisting of chromium, molybdenum tungsten, manganese, rhenium, iron, ruthenium, osmium, nickel, palladium, platinum, copper, silver and gold and mixtures thereof and a ligand having the formula $R_{3-b}L\$_b$ wherein L is trivalent P; each R is independently selected from the group consisting of alkyl, aryl, alkoxyalkyl, aryloxyalkyl, alkoxyaryl, aryloxyaryl, and ferrocenyl groups, wherein the aryl portions thereof can be substituted with a member selected from halogen and hydroxy groups, with the proviso that said halogens on said alkyl groups are not in an alpha-position with respect to said L atom unless they are fluoro atoms; each $ group is indpendently selected from the group consisting of F and $-C\equiv CR$ wherein R is defined as above and b is an integer of from 1 to 3.

2. The complex of claim 1, wherein said transition metal is selected from the group consisting of iron, ruthenium, platinum and mixtures thereof.

3. A complex comprising a carbonyl ligand, a transition metal selected from the group consisting of rhodium and iridium, and mixtures thereof, provided that said rhodium and iridium are in their +1 valence states, and a ligand having the formula $R_{3-b}L\$_b$ wherein L is selected from the group consisting of trivalent P and As; each R is independently selected from the group consisting of alkyl, aryl, alkoxyalkyl, aryloxyalkyl, alkoxyaryl, aryloxyaryl, and ferrocenyl groups, wherein the aryl portions thereof can be substituted with a halogen and the alkyl portions thereof can be substituted with a member selected from halogen and hydroxy groups, with the proviso that said halogens on said alkyl groups are not in alpha-position with respect to said L atom unless they are fluoro atoms; each $ group is independently selected from the group consisting of F and $-C\equiv CR$ wherein R is defined as above and b is an integer of from 1 to 3.

4. The complex of claim 3, wherein said transition metal comprises rhodium in the +1 valence state.

5. The complex according to claim 1 selected from the group consisting of: bis(bis(ferrocenyl)fluorophoshine)tricarbonyliron(O), bis(pentafluorophenyldifluorophosphine)dicarbonylnickel(O), tris(di-tertiary-butylfluorophosphine)tricarbonylmolybdenum, and tris(pentaphenylethynyldifluorophosphine)monocarbonyl triruthenium(O).

* * * * *